(12) United States Patent
Collier et al.

(10) Patent No.: US 10,172,837 B2
(45) Date of Patent: Jan. 8, 2019

(54) INSULIN SENSITISERS AND METHODS OF TREATMENT

(71) Applicant: NAIA Metabolic, Inc., Richmond, CA (US)

(72) Inventors: Gregory Royce Collier, Barwon Heads (AU); Kenneth Russell Walder, Ocean Grove (AU); James Alexander Campbell, Newtown (AU); Juan-Carlos Molero-Navajas, Ocean Grove (AU); Nicky Konstantopoulos, Richmond (AU); Guy Yeoman Krippner, Newtown (AU)

(73) Assignee: Naia Metabolic, Inc., Richmond, CA (US)

( * ) Notice: Subject to any disclaimer, the term of this patent is extended or adjusted under 35 U.S.C. 154(b) by 0 days.

(21) Appl. No.: 15/276,013

(22) Filed: Sep. 26, 2016

(65) Prior Publication Data

US 2017/0079960 A1    Mar. 23, 2017

Related U.S. Application Data

(60) Continuation of application No. 13/907,717, filed on May 31, 2013, now Pat. No. 9,452,148, which is a division of application No. 12/524,146, filed as application No. PCT/AU2008/000089 on Jan. 25, 2008, now Pat. No. 8,455,432.

(60) Provisional application No. 61/007,376, filed on Dec. 11, 2007, provisional application No. 60/984,335, filed on Oct. 31, 2007, provisional application No. 60/897,769, filed on Jan. 25, 2007.

(30) Foreign Application Priority Data

Apr. 17, 2007  (AU) ................. 2007902013

(51) Int. Cl.
| | |
|---|---|
| *A61K 31/433* | (2006.01) |
| *A61K 31/18* | (2006.01) |
| *A61K 31/428* | (2006.01) |
| *A61K 31/155* | (2006.01) |
| *A61K 31/341* | (2006.01) |
| *A61K 31/4035* | (2006.01) |

(52) U.S. Cl.
CPC ........ *A61K 31/433* (2013.01); *A61K 31/155* (2013.01); *A61K 31/18* (2013.01); *A61K 31/341* (2013.01); *A61K 31/4035* (2013.01); *A61K 31/428* (2013.01)

(58) Field of Classification Search
None
See application file for complete search history.

(56) References Cited

U.S. PATENT DOCUMENTS

| | | | |
|---|---|---|---|
| 2,783,241 A | 2/1957 | Young et al. | |
| 2,835,702 A | 5/1958 | Schultz | |
| 3,157,572 A | 11/1964 | Card | |
| 3,668,248 A | 6/1972 | Whitehead et al. | |
| 4,990,523 A | 2/1991 | Nolan et al. | |
| 5,225,424 A | 7/1993 | Schoenwald et al. | |
| 6,214,381 B1 | 4/2001 | Burklow et al. | |
| 7,238,470 B2 | 7/2007 | Hebebrand et al. | |
| 7,375,111 B2 | 5/2008 | Weber et al. | |
| 8,455,432 B2 | 6/2013 | Collier et al. | |
| 9,452,148 B2 | 9/2016 | Collier et al. | |
| 2002/0022245 A1 | 2/2002 | Hebebrand et al. | |
| 2002/0037861 A1 | 3/2002 | Plata-Salaman et al. | |
| 2002/0055458 A1 | 5/2002 | Stefansson | |
| 2003/0060489 A1* | 3/2003 | Buckingham ........ | A61K 31/00 514/342 |
| 2004/0039031 A1 | 2/2004 | Cugnardey et al. | |
| 2005/0037981 A1 | 2/2005 | Beavers et al. | |
| 2005/0288339 A1 | 12/2005 | Takaoka et al. | |
| 2007/0110707 A1 | 5/2007 | Ravi | |
| 2007/0111272 A1 | 5/2007 | Ravi | |
| 2007/0117823 A1 | 5/2007 | Antel et al. | |
| 2011/0003740 A1* | 1/2011 | Collier ................. | A61K 31/18 514/6.5 |
| 2014/0011848 A1 | 1/2014 | Collier et al. | |

FOREIGN PATENT DOCUMENTS

| | | |
|---|---|---|
| CN | 101801375 A | 8/2010 |
| EP | 0749751 A2 | 12/1996 |
| FR | 2468366 A1 | 5/1981 |
| GB | 2223166 A | 4/1990 |
| JP | 2000-80047 A | 3/2000 |
| JP | 2010-516711 A | 5/2010 |

(Continued)

OTHER PUBLICATIONS

Seppala-Lindroos et al. J of Clinical Endocrinology & Metabolism (2002), 87(7):3023-3028.*
Seppala-Lindroos et al. J of Clinical Endocrinology & Metabolism (2002), 87(7):3023-3028. (Previously provided).*
International Search Report, dated Mar. 12, 2008, for PCT Application No. PCT/AU2008/000089, 3 pages.
Written Opinion dated Mar. 12, 2008, for PCT Application No. PCT/AU2008/000089, 7 pages.
"Letters to the Editor. Treatment of Corticosterold-induced Mood Changes With Olanzapine.", Am J Psychiatry, 156 (6)., Jun. 1999, pp. 968-986.

(Continued)

*Primary Examiner* — Yong L Chu
(74) *Attorney, Agent, or Firm* — Dorsey & Whitney LLP

(57) ABSTRACT

The present invention relates generally to the field of therapy. The invention particularly relates to insulin sensitizers and methods of regulating glucose homeostasis and to the therapeutic or prophylactic treatment of diseases and associated conditions, in which impaired glucose uptake due to insulin resistance is involved or implicated, such as diabetes, syndrome X, hyperglycaemia, vascular disease and kidney disease. The present invention further relates to compounds and agents and compositions thereof for use in the treatment methods.

5 Claims, No Drawings

(56) References Cited

FOREIGN PATENT DOCUMENTS

| JP | WO2011/002011 A1 | 1/2011 |
|---|---|---|
| JP | WO2012/008549 A1 | 1/2012 |
| RU | 2268721 C2 | 1/2006 |
| RU | 2350327 C2 | 3/2009 |
| RU | 2356247 C2 | 5/2009 |
| WO | 97/188808 A1 | 5/1997 |
| WO | 01/47509 A2 | 7/2001 |
| WO | 02/03984 A2 | 1/2002 |
| WO | 2002/013800 A2 | 2/2002 |
| WO | 02/051890 A1 | 7/2002 |
| WO | 03/051890 A1 | 6/2003 |
| WO | 03/097045 A1 | 11/2003 |
| WO | 2004/063194 A1 | 9/2004 |
| WO | 2005/025558 A1 | 3/2005 |
| WO | 2005/082414 A2 | 9/2005 |
| WO | 2005/110413 A2 | 11/2005 |
| WO | 2007/030375 A2 | 3/2007 |
| WO | 2007/054580 A1 | 5/2007 |
| WO | 2007/065948 A1 | 6/2007 |
| WO | 2007/114948 A2 | 10/2007 |
| WO | 2008/089521 A1 | 7/2008 |
| WO | 2011/161427 A2 | 12/2011 |

OTHER PUBLICATIONS

Alver, Ahmet et al., "Effects of Leptin and Insulin on CA III Expression in Rat Adipose Tissue", Journal of Enzyme Inhibition and Medicinal Chemistry, 19 (3), Jun. 1, 2004, pp. 279-281.

Alver, Ahmet et al., "The Effect of Carbonic Anhydrase Inhibition on Leptin Secretion by Rat Adipose Tissue", Journal of Enzyme Inhibition and Medicinal Chemistry, 19 (2)., Apr. 1, 2004, pp. 181-184.

Australian Patent Office, International Search Report for International Application No. PCT/AU2008/000089, dated Mar. 12, 2007, 3 pages.

Australian Patent Office, Written Opinion of the International Searching Authority for PCT/AU2008/000089., dated Mar. 12, 2007, 7 pages.

Bernstein, "Diabetes Solution", 2007, "Diabetes Medication: Insulin-Sensitizers & Insulin Mimetics," obtained from http://www.diabetesbook.com/insulin-sensitizers-mimetics/ on Dec. 9, 2016, pp. 1-5.

Biton, Victor, "Clinical Pharmacology and Mechanism of Action of Zonisamide", Clinical Neuropharmacology, 30 (4)., 2007, pp. 230-240.

Boquist et al., "Effects of acetazolamide on insulin release, serum glucose and insulin, glucose tolerance, and alloxan sensitivity of mice.", Med. Biol., 58 (30), Jun. 1980, pp. 169-173.

Carlsson et al., "Effects of the carbonic anhydrase inhibitor acetazolamide on splanchnic blood flow in anaesthetized rats.", Acta Diabetol, 35, 1998, pp. 215-219.

Chernykh et al., "Hypo Glycemic Activity of Aromatic Sulfo Hudrazides and Their Derivatives", Database Biosis (Online), Biosciences Information Service, Philadelphia, PA US. XP002575479. Database accession No. PREV198070053022., 1979, 1 page.

Chernykh, "Per Oral Sucrose Reducing Solfamides", Database Biosis (Online), Biosciences Information Service, Philadelphia, PA, US. XP 00257478, Database accession No. PREV198121050915, 1980, 2 pages.

Corbett, Alastair et al., "Effect of Acetazolamide on Insulin Sensitivity in Myotonic Disorders.", Arch. Neurol., 41., Jul. 1984, pp. 740-743.

Cote, Claude et al., "Effect of carbonic anhydrase in inhibition on substrate utilization and fatigue in", Can. J. Physiol. Parmacol., 71., 1993, pp. 277-283.

Das et al., "Effect of acetazolamide on insulin sensitivity in dogs with alloxan diabetes.", Indian J. Physiol. Pharmacol., 22(3)., 1978, pp. 301-304.

De Simone et al., "Antiobesity Carbonic Anhydrase Inhibitors", Current Topics in Medicinal Chemistry, (2007), 7:879-884.

De Simone et al., "Carbonic anhydrase inhibitors, Zonisamide is an effective inhibitor of the cytosolic isozyme II and mitochondrial isozyme V: solution and X-ray crystallographic studies", Bioorganic & Medicinal Chemistry Letters, (2005), 15:2315-2320.

De Simone, Giuseppina et al., "Antiobesity Carbonic Anhydrase Inhibitors", Current Topics in Medicinal Chemistry, 7 (9)., 2007, pp. 879-884.

Demarest et al., "Glucose Tolerance In Animal Models Of Type 2 Diabetes Mellitus Given Topiramate", Institute of Electronics, Information and Communication Engineers Technical report A226, 44., 2001, 1 page.

Dodgson, Susanna J. et al., "Inhibition of CA V Decreases Glucose Synthesis from Pyruvate", Archives of Biochemistry and Biophysics, 251 (1)., Jul. 28, 1986, pp. 198-204.

Eliasson, B. et al., "Weight loss and metabolic effects of topiramate in overweight and obese type 2 diabetic patients: randomized double-blind placebo-controlled trial", International Journal of Obesity, 31., Feb. 13, 2007, pp. 1140-1147.

Frigerio, Francesca et al., "The antiepileptic drug topiramate preserves metabolism-secretion coupling in insulin secreting cells chronically exposed to the fatty acid oleate", Biochemical Pharmacology, 72., Jul. 17, 2006, pp. 965-973.

Fujikawa—Adachi, Kiyomi et al., "Human Mitochondrial Carbonic Anhydrase VB", The Journal of Biological Chemistry, 274 (30)., Apr. 7, 1999, pp. 21228-21233.

Gabrielsson et al., "Partial Genome Scale Analysis of Gene Expression in Human Adipose Tissue Using DNA Array", Obesity Research, 8 (5)., Feb. 14, 2000, pp. 374-384.

Gadde, Kishore M. et al., "Combination Therapy of Zonisamide and Bupropion for Weight Reduction in Obese Women: A preliminary, Randomized, Open-Label Study", J. Clin. Psychiatry, 68 (8)., Nov. 27, 2006, pp. 1226-1229.

Gadde, Kishore M. et al., "Zonisamide for Weight Loss in Obese Adults. A Randomized Controlled Trial.", JAMA, 289 (14)., Apr. 9, 2003, pp. 1820-1825.

Golay, "Metformin and body weight", International Journal of Obesity, (2008), 32(1):61-72.

Grossman et al., "Effects of Azetazoleamide (Diamox) Upon Blood Sugar of Normal and Diabetic Patients", Proceedings of the Society for Experimental Biology & Medicine, (1956), 93:255-256.

Ha, E. et al., "Topiramate stimulates glucose transport through AMP-activated protein kinase-mediated pathway in L6 skeletal muscle cells", The Pharmacogenomics Journal, 6., Jan. 17, 2006, pp. 327-332.

Hazen, Stacy A., "Differentiation-dependent expression of CA V and the role of carbonic anhydrase isozymes in pyruvate carboxylation in adipocytes.", The FASEB Journal, 10., 1996, pp. 481-490.

Hoskins, Beth et al., "Hyperkalemic Periodic Paralysis", Arch. Neurol, 32., Sep. 17, 1974, pp. 519-523.

Inada, Akari et al., "Timing and Expression Pattern of Carbonic Anhydrase II in Pancreas", Developmental Dynamics, 235., Feb. 14, 2006, pp. 1571-1577.

Johnsen, T., "Effect Upon Serum Insulin, Glucose And Potassium Concentrations Of Acetazolamide During Attacks Of Familial Periodic Hypokalemic Paralysis", Acta. Neurol. Scand., 56., 1977, pp. 533-541.

Kurakazu et al., "Two Cases of Acetazolamide Treatment of Cystoid Macular Edema Secondary to Retinal Vascular Disorder treated with Acetazolamide", Toyooka Hospital, Research Paper No. 10:63-66, 1988.

Lalonde, Josee et al., "Additive effects of leptin and topiramate in reducing fat deposition in lean and obese ob/ob mice", Physiology & Behavior, 80., Aug. 22, 2003, pp. 415-420.

Lean et al., "Waist Circumference as a measure for indicating need for weight management", BMH, (1995), 311:158-161.

Liang et al., "Topiramate ameliorates hyperglycaemia and improves glucose-stimulated insulin release in ZDF rats and db/db mice", Diabetes, Obesity and Metabolism, (2005), 7:360-369.

Lynch, Christopher J. et al., "Carbonic Anhydrase III in obese Zucker rats", Am. J. Physiol (Endocr: Metab. 27), 264., 1993, pp. E621-E630.

(56) References Cited

OTHER PUBLICATIONS

Lynch, Christopher J., "Differentiation-dependent expression of carbonic anhydrase II and III in 3T3 adipocytes.", Am. J. Physiol. (Cell Pysiol. 34), 265., 1993, pp. C234-C243.

Lynch, Chrstopher J. et al., "Role of hepatic carbonic anhydrase In de novo lipogenesis", Biochem. J., 310., 1995, pp. 197-202.

Masereel, Bernard et al., "Carbonic Anhydrase Inhibitors: Anticonvulsant Sulfonamides Incorporating Valproyl and Other Lipophilic Moieties", J. Med. CHem., 45 (2)., May 7, 2001, pp. 312-320.

Mcelroy, Susan L. et al., "Zonisamide in the Treatment of Binge-Eating Disorder: An Open-Label, Prospective Trial", J. Clin. Psychiatry, 65., Jun. 30, 2003, pp. 50-56.

Moynihan, John B. , "Acetazolamide-insensitive carbonic anhydrase activities in liver and", Biochem. J., 272., Oct. 16, 1990, pp. 553-556.

Parkkila, Anna-Kaisa et al., "Expression of Carbonic Anhydrase V in Pancreatic Beta Cells Suggests Role for Mitochondrial Carbonic Anhydrase in Insulin Secretion", Journal of Biological Chemistry, 273 (38)., Sep. 18, 1998, pp. 24620-24623.

Pastorekova, Silvia et al., "Carbonic Anhydrases: Current State of the Art, Therapeutic Applications and Future Prospects", Journal of Enzyme Inhibition and Medicinal Chemistry, 19 (3)., Jan. 9, 2004, pp. 199-229.

Picard, Frederic et al., "Topiramate Reduces Energy and Fat Gains in Lean (Fa/?) and Obese (fa/fa) Zucker Rats", Obesity Research, 8 (9)., Dec. 2000, pp. 656-663.

Richard, D. et al., "The effects of topiramate and sex hormones on energy balance of male and female rats.", International Journal of Obesity, 26., 2002, pp. 344-353.

Saarnio, Juha et al., "Cell-specific Expression of Mitochondrial Carbonic Anhydrase in the Human and Rat Gastrointestinal Tract", The Journal of Histochemistry & Cytochemistry vol. 47 (4)., 1999, pp. 517-524.

Scozzafava, Andrea et al., "Carbonic anhydrase inhibitors and activators and their use in therapy", Expert Opin. Ther. Patent, 16 (12)., 2006, pp. 1627-1664.

Scozzafava, Andrea et al., "Modulation of carbonic anhydrase activity and its applications in therapy", Expert Opin. Ther. Patents, 14 (5)., 2004, pp. 667-702.

Sener, Abdullah et al., "Possible role of carbonic anhydrase in rat pancreatic islets: enzymatic, secretory, metabolic, ionic, and electrical aspects", Am. J. Physiol Endocrinol Metab, 292., 2007, pp. E1624-E1630.

Spicer et al., "Comparative distribution of carbonic anhydrase isozymes III and II in rodent tissues.", Am. J. Anat., 187 (1)., Jan. 1990, pp. 55-64.

Stenlof, K. et al., "Topiramate in the treatment of obese subjects with drug-naive type 2 diabetes", Diabetes, Obesity and Metabolism, 9., 2007, pp. 360-368.

Supuran, Claudiu T. et al., "Applications of carbonic anhydrase inhibitors and activators in therapy", Exp. Opin. Ther. Patents 12 (2)., 2002, pp. 217-242.

Supuran, Claudiu T. et al., "Benzolamide is not a Membrane-impermeant Carbonic Anhydrase Inhibitor", Journal of Enzyme Inhibition and Medicinal Chemistry, 19 (3)., Jan. 9, 2004, pp. 269-273.

Supuran, Claudiu T. et al., "Carbonic anhydrase inhibitors and their therapeutic potential", Exp. Opin. Ther. Patents, 10 (5)., 2000, pp. 575-600.

Supuran, Claudiu T., "Carbonic anhydrase inhibitors in the treatment and prophylaxis of obesity", Expert Opin. Ther. Patents 920030 13 (10)., 2003, pp. 1545-1550.

Supuran, Claudiu T. et al., "Carbonic anhydrases as targets for medicinal chemistry", Bioorg. Med. Chem., 15., Apr. 19, 2007, pp. 4336-4350.

Tamura et al., "Prevention and treatment for development and progression of diabetic macroangiopathy with pioglitazone and metformin", Nippon Rinsho 64 (11)., Nov. 2006, pp. 2119-2125.

Tatematsu, Yoshiyuki et al., "Effect of Acetazolamide on Chronic Macular Edema in Patients with Diabetic Retinopathy", Folia Apthalmol, 52 (3)., 2001, pp. 189-195.

Toplak, H. et al., "Efficacy and safety of topiramate in combination with metformin in the treatment of obese subjects with type 2 diabetes: a randomized, double-blind, placebo-controlled study", International Journal of Obesity, 31., May 16, 2006, pp. 138-146.

Voronina et al., "Some Bio Pharmeceutical Aspects of Butamide Tablets", Database Biosis (Online), Biosciences Information Service, Philadelphia, PA US. XP002575481, Database accession No. PREV197967004692, 1978, 1 page.

Wang, Po W. et al., "Adjunctive zonisamide for weight loss in euthymic bipolar disorder patients: A pilot study", Journal of Psychiatric Research, 42., Apr. 16, 2007, pp. 451-457.

Wilding, J. et al., "A randomized double-blind placebo-controlled study of the long-term efficacy and safety of topiramate in the treatment of obese subjects", International Journal of Obesity, 28., Sep. 21, 2004, pp. 1399-1410.

Wilkes, J. et al., "Topiramate treatment causes skeletal muscle insulin sensitization and increased Acrp30 secretion in high-fat-fed Wistar rats", Am. J. Physiol. Endocrinol. Metab., 289., Jul. 18, 2005, pp. E1015-E1022.

Wilkes, J. et al., "Topiramate is an insulin-sensitizing compound in vivo with direct effects on adipocytes in female ZDF rats", Am. J. Physiol. Endocrinol. Metab., 289., Nov. 9, 2004, pp. E617-E624.

Yoo, Jangsuk et al., "Relationship between insulin resistance and serum alanine aminotransferase as a surrogate of HAFLD (nonalcoholic fatty liver disease) in obese Korean children", Diabetes Research and Clinical Practice, vol. 81, No. 3, 2008, pp. 321-326.

Search Report dated Mar. 22, 2017, in Russian App. No. 2014150946, 2 pages.

\* cited by examiner

INSULIN SENSITISERS AND METHODS OF TREATMENT

This application is a continuation application of U.S. patent application Ser. No. 13/907,717, filed May 31, 2013 (now U.S. Pat. No. 9,452,148, issued Sep. 27, 2016), which is a divisional application of U.S. application Ser. No. 12/524,146, filed Sep. 23, 2010 (now U.S. Pat. No. 8,455,432, issued Jun. 4, 2013), which is a national phase entry under 35 U.S.C. § 371 of International Application No. PCT/AU2008/000089, filed Jan. 25, 2008, which claims priority to U.S. Provisional Application No. 61/007,376, filed Dec. 11, 2007, U.S. Provisional Application No. 60/984,335, filed Oct. 31, 2007, U.S. Provisional Application No. 60/897,769, filed Jan. 25, 2007, and Australian Patent Application No. 2007902013, filed Apr. 17, 2007, the contents of all of which are incorporated herein by reference.

FIELD OF THE INVENTION

The present invention relates generally to the field of therapy. The invention particularly relates to insulin sensitisers and methods of regulating glucose homeostasis and to the therapeutic or prophylactic treatment of diseases and associated conditions, in which impaired glucose uptake due to insulin resistance is involved or implicated, such as diabetes, syndrome X, hyperglycaemia, vascular disease and kidney disease. The present invention further relates to compounds and agents and compositions thereof for use in the treatment methods.

DESCRIPTION OF THE PRIOR ART

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Glucose is the body's preferred energy source. Once entered into the blood stream, it requires the assistance of the insulin to enter hepatic, muscle and adipose cells in order to be stored or utilised. In a healthy individual, glucose homeostasis is controlled primarily by insulin. As blood glucose levels rise, such as after eating, specialised β-cells within the pancreas release insulin which promotes glucose uptake, intracellular metabolism and glycogen synthesis by the body's target tissues. Thus, in healthy individuals, blood glucose concentrations are strictly controlled, typically in the range of 80-110 mg/dl. However, where the pancreas produces an inadequate insulin response, or the target cells do not respond appropriately to the insulin produced, the glucose cannot enter the body's cells. This results in a rapid accumulation of glucose in the blood stream (hyperglycemia).

High blood glucose levels over time may cause cardiovascular disease, retinal damage, renal failure, nerve damage, erectile dysfunction and gangrene (with the risk of amputation). Furthermore, in the absence of available glucose, cells turn to fats as an alternative energy source. Resulting ketones, a product of fat hydrolysis, can accumulate in the blood stream instigating hypotension and shock, coma and even death.

Chronically elevated blood glucose levels (greater than about 126 mg/dl) from either inadequate insulin secretion and/or an inadequate response or sensitivity to insulin is referred to as diabetes, a disease which is now suffered by more than 10 percent of adults in the USA. One of the primary diagnostic features of the diabetic syndrome is the individual's loss of control over glucose homeostasis, so that post-prandial blood glucose levels remain higher for longer after meals, and indeed may remain high for extended periods of time. The disease may be characterised by persistent hyperglycemia, polyuria, polydipsia and/or hyperphagia, chronic microvascular complications such as retinopathy, nephropathy and neuropathy, and macrovascular complications, such as hyperlipidemia and hypertension which can lead to blindness, end-stage renal disease, limb amputation and myocardial infarction. The three most common types of diabetes are type I, type II and gestational.

Type I, known as insulin dependent diabetes mellitus (IDDM), or juvenile-onset diabetes, occurs in 10-15% of all cases. It is most commonly diagnosed in children and adolescents but can occur in young adults as well. It is characterised by β-cell destruction resulting in a loss of insulin secretory function. Most cases relate to autoimmune destruction of the β-cells. Treatment is via insulin injection and must be continued indefinitely.

In contrast, in type II diabetes, known as non-insulin dependent diabetes mellitus (NIDDM) or late-onset diabetes, insulin levels are initially normal but the body's target cells lose their responsiveness to insulin. This is known as insulin resistance or insensitivity. By way of compensation, the pancreas begins to secrete excess insulin, however, in time the pancreas becomes less able to produce enough insulin resulting in chronic hyperglycaemia. Initial symptoms are typically milder than for type I and the condition may go undiagnosed for many years before more severe symptoms present. Lifestyle (poor diet and inactivity) is considered to be a major mediating factor of the condition, although a genetic predisposition increases the risk. Treatment focuses on lifestyle modification, insulin therapy and/or anti-diabetic agents which increase the patient's sensitivity to insulin (insulin sensitisers) or by increasing the patient's production of insulin (insulin secretagogues). Clinical experience has demonstrated that the optimal therapeutic intervention is monotherapy by either an insulin sensitiser or insulin secretagogue, followed by therapies which use a sensitiser and secretagogue in combination.

Gestational diabetes occurs in about 2-5% of all pregnancies. It is temporary, but if untreated may cause foetal complications. Most sufferers make a complete recovery after the birth. However, a proportion of women who develop gestational diabetes go on to develop type II diabetes.

Other, less common, causes of diabetes include genetic defects in n-cells, genetically related insulin resistance, diseases of the pancreas, hormonal defects, malnutrition and chemical or drug influences.

Impaired glucose tolerance and impaired fasting glucose, are pre-type II diabetic states, closely related to type II, and occur when the blood glucose level is higher than normal, but not high enough to be classified as diabetes (about 110-126 mg/dl). As with type II, the body produces insulin but in an insufficient amount or the target tissues are unresponsive to the insulin produced.

Syndrome X, also known as Insulin Resistance Syndrome (IRS) is a cluster of risk factors for heart disease and is associated with insulin resistance. It presents symptoms or risk factors for the development of type II diabetes and heart disease including obesity, atheriosclerosis, hypertriglyceridemia, low HDL cholesterol, hyperinsulinemia, hyperglycaemia, hypertension, impaired glucose tolerance and impaired fasting glucose.

High blood glucose levels and insulin resistance are also associated with fatty liver disease, which can progress to chronic inflammation, fibrosis and cirrhosis.

It is therefore apparent that insulin resistance, or insensitivity, can play a significant role in diabetic and other hyperglycemic-related conditions.

The latest WHO estimate (for the number of people with diabetes, worldwide, in 2003) is 194 million. This is expected to increase to at least 330 million by 2025 and it is estimated that there are around 4 million deaths per year are related to the disorder.

Metformin, a member of the biguanide class of compounds, is an antihyperglycaemic agent which improves glucose tolerance in patients with type II diabetes, lowering both basal and postprandial plasma glucose. Its pharmacologic mechanisms of action are different from other classes of oral antihyperglycaemic agents. Metformin decreases hepatic glucose production, decreases intestinal absorption of glucose, and improves insulin sensitivity by increasing peripheral glucose uptake and utilization. It is regarded as the oral antihyperglycaemic agent of choice in the treatment of type TI diabetes, either as a monotherapy or in conjunction with other anti-diabetic agents such as sulfonylureas. Whilst there is no fixed dosage rate—dosages are individualised on the basis of effectiveness and tolerance, generally commencing with once or twice daily doses of 500 or 850 mg per day—in general, once treatment regimes are established, dosages of the hydrochloride acid addition salt form for adults are at least about 1500 mg per day (about 1000 mg for paediatric patients 10-16 years). The maximum daily dose is 2550 mg per day (2000 mg for paediatric patients 10-16 years). Daily dosages, particularly towards the higher end of the range, are generally taken 2-3 times per day at dosages of 500, 850 or 1000 mg per tablet. In slow release form, the total dose is taken once daily.

However, the efficacy of metformin diminishes with time and the drug is not without further adverse side effects. The most common of these is gastric upsets, which include diarrhoea, intestinal cramping, nausea and vomiting. Long term and higher doses are also associated with vitamin $B_{12}$ deficiencies. The most serious side effect associated with metformin is lactic acidosis, a rare but serious metabolic complication that can occur due to metformin accumulation. When it occurs, it is fatal in approximately 50% of cases. Reported cases have occurred primarily in patients with significant renal insufficiency. The risk may be decreased by regular monitoring of renal function and use of minimum effective dose. The high doses also increase the risk of patient non-compliance. Metformin is contraindicated in patients with renal disease or dysfunction, or acute or chronic acidosis.

Carbonic anhydrases (CAs) are metalloproteinases which catalyse the vital interconversion between carbon dioxide and bicarbonate. This reaction is critical for numerous physiological mechanisms including respiration and transport of $CO_2$ between metabolising tissues and excretion sites, secretion of electrolytes in a variety of tissues and organs, pH regulation and homeostasis, and several metabolic pathways. CAs are ubiquitous across all kingdoms and α-CAs are present in mammals in at least 15 different isoforms. The various isoforms have broad tissue distribution occurring as cytosolic forms (CAI, CAII, CAIII, CAVII, CAXIII), in mitochondrial form (CAV), as membrane bound isozymes (CAIV, CAIX, CAXII, CAXIV), as a secreted form (CAVI) as well as acatalytic forms. The Zn(II) ion of CAs has been shown to be essential for catalysis.

Carbonic anhydrase inhibitors (CAIs) are well established therapeutic agents, initially as diuretics but primarily in the treatment of glaucoma. In the kidney, inhibition of carbonic anhydrase decreases the resorbtion of sodium bicarbonate by the renal tubules, and increasing excretion of sodium, potassium, bicarbonate, and water (Jackson, E. K. in Goodman and Gilman, The Pharmacological Basis of Therapeutics, 10$^{th}$ Ed. McGraw-Hill, New York 2001). In the eye, inhibition of carbonic anhydrase decreases the formation of bicarbonate in the ciliary body. The co-transport of sodium with bicarbonate is responsible for 70% of sodium that enters the posterior chamber of the eye, and water follows the sodium to form the aqueous humor, reduction of which is necessary in the treatment of glaucoma (Alward, W. L. M., New England Journal of Medicine, 1998 339 1298). Inhibitors may be non-specific, or alternatively, they may be specific for one or more enzyme subtypes. They act by binding to the Zn(II) ion of the enzyme. CAIs can generally be divided into two main classes: the metal complexing anions and the sulfonamides, binding either by substituting the non-protein zinc ligand or adding to the metal coordination sphere. Sulfonamides, bearing an unsubstituted sulfonamide group ($-SO_2NH_2$), have been shown to act by binding, in the deprotonated state, in a tetrahedral geometry of the Zn (II) ion, whereby the nitrogen atom of the sulphonamide is coordinated to Zn(II) and the hydrogen of the NH moiety and one of the oxygen atoms participate in hydrogen bonding with the protein.

There is considerable evidence in the literature that the carbonic anhydrase isozymes play a critical role in energy metabolism. In the early 1900's, Krebs identified CA as the enzyme which facilitated the incorporation of carbon dioxide into the gluconeogenesis pathway. The CA isozyme V was identified as being localised in the mitochondria. In subsequent research CA was identified as having a role in lipogenesis, (Lynch, C. J. et al, Biochem. J., 1995, 310, 197 and Faseb, J., 1996, 10, 481) and claims have been made as to the utility of carbonic anhydrase inhibitors in the treatment of obesity (US 20020022245).

US 20020022245 teaches the use of CAIs, as a general class of compounds, in the treatment or prevention of obesity. The compounds are described as inhibitors of de novo lipogenesis, with topiramate described as a specific example. Whilst there may be a causal link between obesity and diabetes, and treatment of obesity may have ameliorating flow-on effects on the symptoms of diabetic conditions through loss of body weight, these flow-on effects are only observed after treatment for several weeks and only occur subsequent to loss of significant body weight.

However, it is noted that there has been limited translation of anti-obesity pharmaceuticals from animal models to pharmaceuticals that have received regulatory approval for marketing, and that for the few anti-obesity therapies that are available for prescription there are side effects and limited clinical benefit associated with their use.

Given the prevalence of diabetes and other diseases and conditions with which insulin resistance is associated, and their potential consequences, there remains, the need for new therapeutic protocols for the treatment and/or prevention of conditions in which insulin resistance or elevated blood glucose levels are a causative or contributing factor.

SUMMARY OF THE INVENTION

It has now been surprisingly found that certain compounds which have CA inhibitory activity act to regulate or modulate blood glucose levels. Without limiting by theory, carbonic anhydrase inhibitors (CAIs), may improve or ameliorate insulin resistance in cells, such as adipocytes and skeletal muscle cells, effectively resensitising the cells to the action of insulin and thereby enabling a reduction in elevated blood glucose levels. Such compounds may have therapeutic utility in the treatment or prevention of diseases, and associated conditions and symptoms, in which insulin resistance is implicated by providing direct control over the blood glucose levels for patients that are diabetic or pre-diabetic. The cellular response to the CAIs occurs rapidly and is not dependent on changes in cellular lipid content.

It has further been found that some CAIs which are also loop diuretics or thiazide diuretics, do not provide a similar benefit in vivo.

Accordingly, the present invention is directed to the use of sulfonamide compounds, or their isosteres, which are carbonic anhydrase inhibitors, as insulin sensitisers in the regulation of blood glucose levels (i.e. glucose homeostasis) and the treatment or prevention of diabetes and related conditions, provided that they are not also loop or thiazide diuretics. Furthermore, the CAI is not topiramate or zonisamide.

Accordingly, one aspect of the present invention thus provides a method of increasing glucose uptake by a cell comprising contacting said cell with a carbonic anhydrase inhibitor compound which is a sulfonamide ($-SO_2NH_2$) compound, or an isostere thereof, or a pharmaceutically acceptable salt, solvate or prodrug thereof;

provided that the compound is not also a loop diuretic or thiazide diuretic, and further provided that the compound is not topiramate or zonisamide.

Methods for increasing glucose uptake by a cell, for example adipocytes or muscle and hepatic cells, can be performed in vivo or in vitro.

Advantageously, the compounds contemplated by the invention may result in the lowering of elevated blood glucose levels, and thereby may have utility in the treatment of insulin resistance and diseases or conditions in which insulin resistance is implicated. The compounds contemplated by the present invention may also have utility in maintaining normal fasting state blood glucose levels in patients who yet do not display diabetic or pre-diabetic blood glucose levels and thus may prevent or delay the development of a diabetic or pre-diabetic condition in a patient who, for example, may be pre-disposed to such a condition by familial history or lifestyle factors.

Thus, in another aspect, the present invention is directed to a method of lowering elevated or maintaining normal blood glucose levels in a subject in need thereof, comprising administering to said subject a carbonic anhydrase inhibitor compound which is a sulfonamide ($-SO_2NH_2$) compound, or an isostere thereof, or a pharmaceutically acceptable salt, solvate or prodrug thereof;

provided that the compound is not also a loop diuretic or thiazide diuretic, and further provided that the compound is not topiramate or zonisamide.

Yet a further aspect of the invention provides a method for treating a disease or condition, or symptom thereof, in which insulin resistance is involved, in a subject in need thereof, comprising administering to said subject a carbonic anhydrase inhibitor compound which is a sulfonamide ($-SO_2NH_2$) compound, or an isostere thereof, or a pharmaceutically acceptable salt, solvate or prodrug thereof;

provided that the compound is not also a loop diuretic or thiazide diuretic, and further provided that the compound is not topiramate or zonisamide.

In certain embodiments of the invention, the disease or condition is type TI diabetes, gestational diabetes, impaired glucose tolerance, impaired fasting glucose or syndrome X.

Further aspects of the invention provide a carbonic anhydrase inhibitor compound which is a sulfonamide ($-SO_2NH_2$) compound, or an isostere thereof, or a pharmaceutically acceptable salt, solvate or prodrug thereof; for use in therapy, particularly for regulating glucose homeostasis, treating insulin resistance, and/or treating a disease or condition, or one or more symptoms thereof, in which insulin resistance is involved, provided that the compound is not also a loop diuretic or thiazide diuretic, and further provided that the compound is not topiramate or zonisamide.

The present invention also provides for agents and compositions for treating insulin resistance, lowering elevated or maintaining normal blood levels and/or treating a disease or condition, or one or more symptoms thereof, in which insulin resistance is involved, comprising carbonic anhydrase inhibitor compound which is a sulfonamide ($-SO_2NH_2$) compound, or an isostere thereof, or a pharmaceutically acceptable salt, solvate or prodrug thereof;

provided that the compound is not also a loop diuretic or thiazide diuretic, and further provided that the compound is not topiramate or zonisamide and for the use of such a compound in the manufacture of medicaments therefor.

The subjects to be treated in accordance with the invention may be selected on the basis of requiring said treatment by the CAI compounds contemplated by the invention, i.e. the CAI compounds are administered for the purpose of increasing glucose uptake, treating insulin resistance, lowering elevated or maintaining normal blood levels and/or treating a disease or condition, or one or more symptoms thereof, in which insulin resistance is involved.

In certain embodiments of the invention, the CAI is used as an insulin sensitiser in monotherapy, i.e. the CAI is essentially the only active agent administered in order to achieve the desired therapeutic effect. In other embodiments of the invention, the CAI is used as an insulin sensitiser in combination with one or more other anti-diabetic agents such as insulin secretagogues. In still other embodiments of the invention, the CAI is used in combination with metformin, or its pharmaceutically acceptable salts.

In some particular embodiments of the invention, the CAI is methazolamide or an analogue thereof, or pharmaceutically acceptable salts thereof. In further examples of this embodiment, the methazolamide is administered in a regime in combination with metformin or its pharmaceutically acceptable salts.

Thus, in still further embodiments of the invention there is provided a combination comprising metformin, or a pharmaceutically acceptable salt thereof, and methazolamide or methazolamide analogue, or a pharmaceutically acceptable salt thereof.

The combination of the invention may be administered as a single composition of the two agents or may comprise each agent as an individual component. Where the active agents are administered as individual components, they may be administered sequentially or simultaneously.

DETAILED DESCRIPTION OF THE INVENTION

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

The singular forms "a", "an" and "the" include plural aspects unless the context clearly dictates otherwise.

The compounds contemplated by the present invention are sulfonamide compounds, or their isosteres, which have carbonic anhydrase inhibitory activity, i.e. are capable of inhibiting at least one carbonic anhydrase in mammals, for example at least one human carbonic anhydrase, such as those isoforms hereinbefore discussed. The compounds may have inhibitory activity against a number of CA subtypes (isoforms) or may inhibit only one CA subtype or a defined group of subtypes, i.e. demonstrate a selectivity or affinity for one or more subtypes in preference to others. In certain embodiments of the invention, the compounds exhibit a selectivity or affinity for isoform V over other isoforms. However, it should be noted that although the compounds contemplated herein may be conveniently classified on the basis of having carbonic anhydrase inhibitory activity, this may or may not be the mechanism by which the compounds achieve the described therapeutic effects.

The term "isostere" such as when used in reference to the sulfonamide group, refers to a functional group with the same physiochemical properties required for the desired activity, which may include electronegatitivity, steric, size, lipophilicity and in particular, for the sulfonamide (—SO$_2$NH$_2$) group zinc binding ability. Like the unsubstituted —SO$_2$NH$_2$ group, the isosteres contemplated herein are capable of binding to the Zn of the CA enzyme. Examples of isosteres of sulfonamides include the groups: —SO$_2$NHOH, —SO$_2$NHSH, —SO$_2$NHCN, —SO$_2$NHNH$_2$, —SO$_2$NH—1-imidazolyl, —SO$_2$NHPO$_3$H$_2$, —SO$_2$NHSO$_2$NH$_2$, —SO$_2$NHSO$_2$OH. —OSO$_2$NH$_2$— OSO$_2$NHOH, —OSO$_2$NHPO$_3$H$_2$, —OSO$_2$NHSO$_2$NH$_2$, —OSO$_2$NHSO$_2$OH, —NSO$_2$NH$_2$, —NSO$_2$NHOH, —NSO$_2$NHPO$_3$H$_2$, —NSO$_2$NHSO$_2$NH$_2$, —NSO$_2$NHSO$_2$OH, =NSO$_2$NH$_2$, —NHCONH$_2$, —ONHCONH$_2$ and —ONHCOR, where R is H or C$_{1-6}$alkyl.

Compounds which are CAIs are well known in the art, see for example, Pastorekova et al, *Journal of Enzyme Inhibition and Medicinal Chemistry*, 19(3), 199-229, 2004. Methods for determining the carbonic anhydrase inhibitory activity of a compound, i.e. whether a compound can be classified as a CAI, are known in the art and may usefully identify further compounds which may be suitable for use in the present invention. Exemplary methods and levels of activity required for consideration as CAIs are described in US 20020022245 and the references cited therein, the contents of which are incorporated herein by reference, in particular Supuran et al, *European Journal of Medicinal Chemistry*, 1998, 33, 577-594 and Scozzafava et al, *Journal of Medicinal Chemistry*, 1999, 42 25, 3690-3700).

A number of known CAIs are depicted below in Table A.

TABLE A

Known Inhibitors of Carbonic Anhydrase

| Compound | IC$_{50}$ (nM) | Reference |
|---|---|---|
| Dichlorphenamide | 38 | Nishimori et al Journal of Medicinal Chemistry (2005), 48(24), 7860-7866. |
| Zonisamide | 35 | Teperini et al Bioorganic & Medicinal Chemistry (2007) |
| Sulpiride | 40 | Nishimori et al Journal of Medicinal Chemistry (2005), 48(24), 7860-7866. |
| Methazolamide | 14 | Nishimori et al Journal of Medicinal Chemistry (2005), 48(24), 7860-7866. |
| 2-aminobenzenesulfonamide | 295 | Nishimori et al Journal of Medicinal Chemistry (2005), 48(24), 7860-7866. |
| Furosemide | 80 | Supuran et al European Journal of Medicinal Chemistry (1997) 32 311 |
| Chlorothiazide | 460 | Supuran et al European Journal of Medicinal Chemistry (1997) 32 311 |
| Chlorthalidone | 260 | Iyer et al Journal of Biomolecular Screening (2006) 11 782 |
| Ethoxyzolamide | 8 | Nishimori et al Journal of Medicinal Chemistry (2005), 48(24), 7860-7866. |
| Dorzolamide | 9 | Nishimori et al Journal of Medicinal Chemistry (2005), 48(24), 7860-7866. |
| Acetazolamide | 12 | Nishimori et al Journal of Medicinal Chemistry (2005), 48(24), 7860-7866. |

Compounds from which the sulfonamides or isosteres having CA inhibitory activity may be selected may be defined by Formula (I):

$$A\text{-}W\text{—}X \qquad (I)$$

wherein
X is SONH$_2$ or an isostere thereof;
W is a direct bond between A and X, or an alkylene chain of 1 to 5 carbon atoms, wherein a CH$_2$ group may be replaced by O, S or NH;
A is a group selected from alkyl, alkenyl, alkynyl, aryl, arylalkyl, heteroaryl, heteroarylalkyl, carbocyclyl, carbocyclylalkyl, heterocyclyl, and heterocyclylalkyl, each of which may be optionally substituted.

As used herein, the term "alkyl", used either alone or in compound words, denotes straight chain, or branched saturated hydrocarbon residues, preferably C$_{1-20}$ alkyl, e.g. C$_{1-10}$ or C$_{1-6}$. Some examples of straight chain and branched alkyl include methyl, ethyl, n-propyl, isopropyl, n-butyl, sec-butyl, t-butyl, n-pentyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, and decyl. Where an alkyl group is referred to generally as "propyl", butyl" etc, it will be understood that this can refer to any of straight or branched isomers where appropriate. An alkyl group may be optionally substituted by one or more optional substituents as herein defined.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4,pentadienyl, 1,3-hexadienyl and 1,4-hexadienyl. An alkenyl group may be optionally substituted by one or more optional substituents as herein defined or by replacing up to one, two or three C atoms independently by O, N or S.

The term "alkynyl" denotes groups formed from straight chain or branched hydrocarbon residues containing at least one carbon-carbon triple bond including ethynically mono-, di- or poly-unsaturated alkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined or by replacing up to one, two or three C atoms independently by O, N or S.

The term "aryl" (or "carboaryl)", or the abbreviated form "ar" used in compound words such as "aralkyl", denotes any of mono-, bi- or polcyclic, (including conjugated and fused) hydrocarbon ring systems containing an aromatic residue. Examples of aryl include phenyl, biphenyl, terphenyl, quaterphenyl, naphthyl, tetrahydronaphthyl (tetralinyl), anthracenyl, dihydroanthracenyl, benzanthracenyl, dibenzanthracenyl, phenanthrenyl, fluorenyl, pyrenyl, idenyl, isoindenyl, indanyl, azulenyl and chrysenyl. Particular examples of aryl include phenyl and naphthyl. An aryl group may be optionally substituted by one or more optional substituents as herein defined.

The term "carbocyclyl" includes any of non-aromatic monocyclic, bicyclic and polycyclic, (including fused, bridged or conjugated) hydrocarbon residues, e.g. $C_{3-20}$ (such as $C_{3-10}$ or $C_{3-8}$). The rings may be saturated, for example cycloalkyl, or may possess one or more double bonds (cycloalkenyl) and/or one or more triple bonds (cycloalkynyl). Examples of carbocyclyl include monocyclic 5-6-membered or bicyclic 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl and decalinyl. A carbocyclyl group may be optionally substituted by one or more optional substituents as herein defined. A monocarbocyclyl group may be substituted by a bridging group to form a bicyclic bridged group.

The term "heterocyclyl" when used alone or in compound words includes any of monocyclic, bicyclic or polycyclic, (including fuse, bridged or conjugated) hydrocarbon residues, such as $C_{3-20}$ (e.g. $C_{3-10}$ or $C_{3-8}$) wherein one or more carbon atoms are independently replaced by a heteroatom so as to provide a group containing a non-aromatic heteroatom-containing ring. Suitable heteroatoms include, O, N, S, P and Se, particularly O, N and S. Where two or more carbon atoms are replaced, this may be by two or more of the same heteroatom or by different heteroatoms. The heterocyclyl group may be saturated or partially unsaturated, e.g. possess one or more double bonds. Particularly preferred heterocyclyl are monocyclic 5-6- and bicyclic 9-10-membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, 1-, 2- and 3-pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl (tetramethylene sulfide), pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, thiadiazolinyl, azepinyl, oxepinyl, thiepinyl, indenyl, indanyl, 3H-indolyl, isoindolinyl, 4H-quinolazinyl, chromenyl, chromanyl, isochromanyl, benzoxazinyl (2H-1,3, 2H-1,4-, 1H-2,3-, 4H-3, 1-4H-1,4) pyranyl and dihydropyranyl. A heterocyclyl group may be optionally substituted by one or more optional substituents as defined herein.

The term "heteroaryl" includes any of monocyclic, bicyclic, polycyclic, (fused or conjugated) hydrocarbon residues, wherein one or more carbon atoms are replaced by a heteroatom so as to provide a residue having at least one aromatic heteroatom-containing ring. Exemplary heteroaryl have 3-20 ring atoms, e.g. 3-10. Particularly preferred heteroaryl are 5-6 monocyclic and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, benzothiazolyl, isothiazolyl, isoxazolyl, triazolyl, oxadialzolyl, oxatriazolyl, triazinyl, tetrazolyl and furazanyl. A heteroaryl group may be optionally substituted by one or more optional substituents as defined herein.

In this specification "optionally substituted" is taken to mean that a group may be unsubstituted or further substituted or fused (so as to form a condensed bi- or polycyclic group) with one, two, three or more of organic and inorganic groups, including those selected from: alkyl, alkenyl, alkynyl, carbocyclyl, aryl, heterocyclyl, heteroaryl, acyl, aralkyl, alkylaryl, alkylheterocyclyl, alkylheteroaryl, alkylcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroaryl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamido, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterhetcrocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate, sulfonate, phosphonate and phosphate groups. Optional substituents also include =O, =S, =CHR and =NR, i.e. where a $CH_2$ group in a chain or ring is replaced by a carbonyl group (C=O) (oxo), or a thiocarbonyl group (C=S) (thioxo) or a C=CHR or C=NR group, (where R is hydrogen, $C_{1-6}$alkyl, $C_{2-6}$alkenyl, $C_{2-6}$alkynyl, $C_{3-6}$ cycloalkyl, C(O)H, C(O)$C_{1-6}$alkyl, C(O)phenyl, C(O)$NH_2$, C(O)NH$C_{1-6}$alkyl, C(O)NHphenyl, C(O)$(CH_2)_n$phenyl and C(O)NH$(CH_2)_n$phenyl (wherein n is 1-6 and phenyl may be optionally substituted by one or more substituents independently selected from $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$ alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl)), or where 2 adjacent or non-adjacent carbon atoms (e.g. 1,2- or 1,3) are substituted by one end each of a —O—$(CH_2)_s$—O— or —$NR^x$—$(CH_2)_s$—$NR^x$— group, wherein s is 1 or 2 and each $R^x$ is independently H or $C_{1-6}$alkyl, and where 2 adjacent or non-adjacent atoms, independently selected from C and N, are substituted by one end each of a $C_{1-5}$alkylene or $C_{2-5}$alkenylene group (so as to form a bridged group).

Exemplary optional substituents include those selected from: alkyl, (e.g. $C_{1-6}$alkyl such as methyl, ethyl, propyl, butyl), cycloalkyl (e.g. $C_{3-6}$cycloalkyl, such as cyclopropyl, cyclobutyl, cyclopentyl or cyclohexyl), hydroxyalkyl (e.g. hydroxy$C_{1-6}$alkyl, such as hydroxymethyl, hydroxyethyl, hydroxypropyl), alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl), alkoxy (e.g. $C_{1-6}$alkoxy, such as methoxy, ethoxy, propoxy, butoxy), alkoxyalkoxy (e.g. $C_{1-6}$alkocy$C_{1-6}$ alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy) cycloalkoxy (e.g. cyclopropoxy, cyclobutoxy, cyclopentoxyl, cyclohexyloxy), halo, haloalkyl(e.g. halo$C_{1-6}$alkyl, such as chloromethyl, difluoromethyl, trifluoromethyl, trichloromethyl, tribromomethyl), haloalkoxy (e.g. halo$C_{1-6}$ alkoxy), hydroxy, thio (—SH), sulfonyl, sulfonamido, phenyl (which itself may be further substituted e.g., by one or more $C_{1-6}$alkyl, halo, hydroxy, hydroxy$C_{1-6}$alkyl, $C_{1-6}$ alkoxy, $C_{1-6}$alkoxy$C_{1-6}$alkyl, $C_{1-6}$alkoxy$C_{1-6}$alkoxy, halo $C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), benzyl (wherein benzyl itself may be further substituted e.g., by one or more of $C_{1-6}$alkyl, halo, hydroxy, hydroxy$C_{1-6}$alkyl, $C_{1-6}$ alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), phenoxy (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), benzyloxy (wherein benzyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$alkoxy$C_{1-6}$ alkoxy, halo$C_{1-6}$ alkyl, halo$C_{1-6}$alkoxy, cyano, nitro, OC(O) $C_{1-6}$alkyl, $NH_2$, NH$C_{1-6}$alkyl, NHC(O)$C_{1-6}$alkyl and N$C_{1-6}$ alkyl$C_{1-6}$alkyl), $NH_2$, alkylamino (e.g. —NH$C_{1-6}$alkyl, such as methylamino, ethylamino, propylamino etc), dialkylamino (e.g. —NH($C_{1-6}$alkyl)$_2$, such as dimethylamino, diethylamino, dipropylamino), acylamino (e.g. —NHC(O) $C_{1-6}$alkyl, such as —NHC(O)$CH_3$), diacylamino, phenylamino (i.e. —NHphenyl, wherein phenyl itself may be further substituted e.g., by one or more of $C_{1-6}$alkyl, halo, hydroxy, hydroxy$C_{1-6}$alkyl, hydroxy$C_{1-6}$ alkoxy $C_{1-6}$ alkoxy, $C_{1-6}$alkoxy$C_{1-6}$alkylalkoxy$C_{1-6}$alkyl, $C_{1-6}$alkoxy $C_{1-6}$ alkoxy, halo$C_{1-6}$alkyl, halo$C_{1-6}$ alkoxy, cyano, nitro, OC(O)$C_{1-6}$alkyl, $NH_2$, NH$C_{1-6}$alkyl, NHC(O)$C_{1-6}$alkyl and N$C_{1-6}$ alkyl$C_{1-6}$alkyl), nitro, cyano, formyl, —C(O)-alkyl (e.g. —C(O)$C_{1-6}$alkyl, such as acetyl), O—C(O)-alkyl (e.g. —OC(O)$C_{1-6}$alkyl, such as acetyloxy), benzoyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$ alkyl), benzoyloxy (wherein benzyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$ alkoxy$C_{1-6}$ alkoxy, halo$C_{1-6}$alkyl, halo$C_{1-6}$alkoxy, cyano, nitro, OC(O) $C_{1-6}$alkyl, $NH_2$, NH$C_{1-6}$alkyl, NHC(O)$C_{1-6}$alkyl and N$C_{1-6}$ alkyl$C_{1-6}$alkyl), $CO_2H$, $CO_2$alkyl (e.g. $CO_2C_{1-6}$ alkyl such as methyl ester, ethyl ester, propyl ester, butyl ester), $CO_2$phenyl (wherein phenyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$alkoxy$C_{1-6}$ alkoxy, halo$C_{1-6}$alkyl, halo$C_{1-6}$alkoxy, cyano, nitro, OC(O) $C_{1-6}$alkyl, $NH_2$, NH$C_{1-6}$alkyl. NHC(O)$C_{1-6}$alkyl and N$C_{1-6}$ alkyl$C_{1-6}$alkyl), $CO_2$benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$ alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O) $C_{1-6}$alkyl and N$C_{1-6}$alkyl$C_{1-6}$alkyl), $CONH_2$, C(O)NHphenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$ alkyl, halo$C_{1-6}$alkoxy, cyano, nitro, OC(O)$C_{1-}$ ₆alkyl, NH₂, NHC₁₋₆alkyl, NHC(O)C₁₋₆ alkyl and NC₁₋₆alkylC₁₋₆alkyl), C(O)NHbenzyl (wherein benzyl itself may be further substituted e.g., by one or more of C₁₋₆alkyl, halo, hydroxy, hydroxyC₁₋₆alkyl, C₁₋₆alkoxy, C₁₋₆ alkoxyC₁₋₆alkyl, C₁₋₆alkoxyC₁₋₆alkoxy, haloC₁₋₆alkyl, haloC₁₋₆alkoxy, cyano, nitro, OC(O)C₁₋₆alkyl, NH₂, NHC₁₋₆alkyl, NHC(O)C₁₋₆alkyl and NC₁₋₆alkylC₁₋₆alkyl), C(O)NHalkyl (e.g. C(O)NHC₁₋₆ alkyl such as methyl amide, ethyl amide, propyl amide, butyl amide) C(O)Ndialkyl (e.g. C(O)N(C₁₋₆alkyl)₂) aminoalkyl (e.g., HNC₁₋₆alkyl-, C₁₋₆ alkylHN—C₁₋₆alkyl- and (C₁₋₆alkyl)₂N—C₁₋₆alkyl-), thioalkyl (e.g., HSC₁₋₆alkyl-), carboxyalkyl (e.g., HO₂CC₁₋₆ alkyl-), carboxyesteralkyl (e.g., C₁₋₆alkylO₂CC₁₋₆alkyl-), amidoalkyl (e.g., H₂N(O)CC₁₋₆alkyl-, H(C₁₋₆alkyl)N(O)CC₁₋₆alkyl-), formylalkyl (e.g., OHCC₁₋₆alkyl-), acylalkyl (e.g., C₁₋₆alkyl(O)CC₁₋₆alkyl-), nitroalkyl (e.g., O₂NC₁₋₆alkyl-), oxo (=O), thioxo (=S), =CHR, imino (=NR), substitution of 2 adjacent or non-adjacent carbon atoms (e.g. 1,2 or 1,3) by one end each of a —O—(CH₂)ₛ—O— or —NR'—(CH₂)ₛ—NR'— group, wherein s is 1 or 2 and each R' is independently H or C₁₋₆alkyl, and substitution of 2 adjacent or non-adjacent atoms, independently selected from C and N, by a C₂₋₅alkylene or C₂₋₅alkenylene group.

Terms written as "[group]oxy" refer to a particular group when linked by oxygen, for example, the terms "alkoxy", "alkenoxy", "alkynoxy" and "aryloxy" and "acyloxy" respectively denote alkyl, alkenyl, alkynyl, aryl and acyl groups as hereinbefore defined when linked by an oxygen atom. Terms written as "[group]thio" refer to a particular group when linked by sulfur, for example, the terms "alkylthio", "alkenylthio", alkynylthio" and "arylthio" respectively denote alkyl, alkenyl, alkynyl, aryl groups as hereinbefore defined when linked by a sulfur atom. Similarly, a term written as "[groupA]groupB" is intended to refer to a groupA when linked by a divalent form of groupB, for example, "hydroxyalkyl" is a hydroxy group when linked by an alkylene group and "arylalkyl" is an aryl group when linked by an alkylene group.

The term "halogen" ("halo") denotes fluorine, chlorine, bromine or iodine (fluoro, chloro, bromo or iodo).

The term "acyl" either alone or in compound words denotes a group containing the moiety C=O (and not being a carboxylic acid, ester or amide) Preferred acyl includes C(O)—R, wherein R is hydrogen or an alkyl, alkenyl, alkynyl, aryl, heteroaryl, carbocyclyl, or heterocyclyl residue. Examples of acyl include formyl, straight chain or branched alkanoyl (e.g. C₁₋₂₀) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl). The R residue may be optionally substituted as described herein.

The term "sulfoxide", either alone or in a compound word, refers to a group —S(O)R wherein R is selected from hydrogen, alkyl, alkenyl, alkynyl, aryl, heteroaryl, heterocyclyl, carbocyclyl, and aralkyl. Examples of R include hydrogen, C₁₋₂₀alkyl, phenyl and benzyl.

The term "sulfonyl", either alone or in a compound word, refers to a group S(O)₂—R, wherein R is selected from hydrogen, alkyl, alkenyl, alkynyl, aryl, heteroaryl, heterocyclyl, carbocyclyl, acyl, and aralkyl. Examples of R include hydrogen, C₁₋₂₀alkyl, phenyl and benzyl.

The term "sulfonamide", or "sulfonamyl" of "sulfonamido", either alone or in a compound word, refers to a group S(O)₂NRR wherein each R is independently selected from hydrogen, alkyl, alkenyl, alkynyl, aryl, heteroaryl, heterocyclyl, carbocyclyl, acyl, and aralkyl. Examples of R include hydrogen, C₁₋₂₀alkyl, phenyl and benzyl. In an embodiment at least one R is hydrogen. In another form, both R are hydrogen.

A "sulfate" group refers to a group —OS(O)₂OR wherein each R is independently selected from hydrogen, alkyl, alkenyl, alkynyl, aryl, heteroaryl, heterocyclyl, carbocyclyl, acyl, and aralkyl. Examples of R include hydrogen, C₁₋₂₀alkyl, phenyl and benzyl.

The term "sulfonate" refers to a group SO₃R wherein each R is independently selected from hydrogen, alkyl, alkenyl, alkynyl, aryl, heteroaryl, heterocyclyl, carbocyclyl, acyl, and aralkyl. Examples of R include hydrogen, C₁₋₂₀alkyl, phenyl and benzyl.

The term "thio" is intended to include groups of the formula "—SR" wherein R can be hydrogen (thiol), alkyl, alkenyl, alkynyl, aryl, carbocyclyl, heteroaryl, heterocyclyl, aralkyl, and acyl. Examples of R include hydrogen, C₁₋₂₀alkyl, phenyl and benzyl.

The term, "amino" is used here in its broadest sense as understood in the art and includes groups of the formula —NR$^A$R$^B$ wherein R$^A$ and R$^B$ may be any independently selected from hydrogen, hydroxy alkyl, alkoxyalkyl, alkenyl, alkynyl, aryl, carbocyclyl, heteroaryl, heterocyclyl, aralkyl, acyl and amido, each of which may be optionally substituted. R$^A$ and R$^B$, together with the nitrogen to which they are attached, may also form a monocyclic, or polycyclic ring system e.g. a 3-10 membered ring, particularly, 5-6 and 9-10 membered systems. Examples of "amino" include —NH₂, —NHalkyl (e.g. —NHC₁₋₂₀alkyl), —NHalkoxyalkyl, —NHaryl (e.g. —NHphenyl), —NHaralkyl (e.g. —NHbenzyl), —NHacyl (e.g. —NHC(O)C₁₋₂₀alkyl, —NHC(O)phenyl), —NHamido, (e.g. NHC(O)NHC₁₋₆ alkyl, NHC(O)NH phenyl), —Ndialkyl (wherein each alkyl, for example C₁₋₂₀, may be the same or different) and 5 or 6 membered rings, optionally containing one or more same or different heteroatoms (e.g. O, N and S). Reference to groups written as "[group]amino" is intended to reflect the nature of the R$^A$ and R$^B$ groups. For example, "alkylamino" refers to —NR$^A$R$^B$ where one of R$^A$ or R$^B$ is alkyl. "Dialkylamino" refers to —NR$^A$R$^B$ where R$^A$ and R$^B$ are each (independently) an alkyl group.

The term "amido" is used here in its broadest sense as understood in the art and includes groups having the formula C(O)NR$^A$R$^B$, wherein R$^A$ and R$^B$ are as defined as above. Examples of amido include C(O)NH₂, C(O)NHalkyl (e.g. C₁₋₂₀alkyl), C(O)NHaryl (e.g. C(O)NHphenyl), C(O)NHaralkyl (e.g. C(O)NHbenzyl), C(O)NHacyl (e.g. C(O)NHC(O)C₁₋₂₀alkyl, C(O)NHC(O)phenyl), C(O)Nalkylalkyl (wherein each alkyl, for example C₁₋₂₀, may be the same or different) and 5 or 6 membered rings, optionally containing one or more same or different heteroatoms (e.g. O, N and S).

The term "carboxy ester" is used here in its broadest sense as understood in the art and includes groups having the formula —CO₂R, wherein R may be selected from groups including alkyl, alkenyl, alkynyl, aryl, carbocyclyl, heteroaryl, heterocyclyl, arylalkyl, heteroarylalkyl, carbocyclylalkyl, heterocyclylalkyl, aralkenyl, heteroarylalkenyl, carbocyclylalkenyl, heterocyclylalkenyl, aralkynyl, heteroarylalkynyl, carbocyclylalkynyl, heterocyclylalkynyl, and acyl, each of which may be optionally substituted. Some examples of carboxy ester include —CO$_2$C$_{1-20}$alkyl, —CO$_2$aryl (e.g. —CO$_2$phenyl), —CO$_2$arC$_{1-20}$ alkyl (e.g. —CO$_2$ benzyl).

The term "phosphonate" refers to a group —P(O)(OR$_2$) wherein R is independently selected from hydrogen, alkyl, alkenyl, alkynyl, aryl, heteroaryl, heterocyclyl, carbocyclyl, acyl, and aralkyl. Examples of R include hydrogen, C$_{1-20}$alkyl, phenyl and benzyl.

The term "phosphate" refers to a group —OP(O)(OR)$_2$ wherein R is independently selected from hydrogen, alkyl, alkenyl, alkynyl, aryl, heteroaryl, heterocyclyl, carbocyclyl, acyl, and aralkyl. Examples of R include hydrogen, C$_{1-20}$alkyl, phenyl and benzyl.

In some examples of Formula (I), A is a monocyclic or bicyclic heterocyclyl or heteroaryl group which may be optionally substituted as defined herein.

It has further surprisingly been found that certain sulfonamide compounds which are inhibitors of CA, but also act as "loop" or "thiazide" diuretics, do not demonstrate the desired activity in an in vivo model. Such compounds are excluded from consideration in the present invention.

The loop diuretics so named because they act on the Na$^+$K$^+$(Cl$^-$)$_2$ symporter in the ascending loop of Henle in the kidney, act to inhibit sodium and chloride reabsorption. Loop diuretics also cause vasodilation of the veins and of the kidney's blood vessels, mechanically causing a decrease in blood pressure. They are therefore primarily used to treat hypertension and edema, often due to congestive heart failure or renal insufficiency. The skilled person will recognise and understand which compounds are also loop diuretics. Examples of loop diuretics which are excluded from the scope of the present invention include furosemide, torsemide, bumetanide, azosemide and piretanide.

Some compounds which are known to be loop diuretics, can be generalised by the formula:

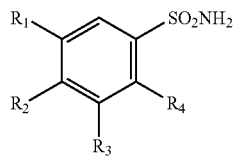

wherein

R$_1$ is an ionic moiety or isostere, such as carboxylate, tetrazolyl, sulfonate or phosphate;

R$_2$ is a hydrophobic moiety such as halo, alkyl, phenyl, alkoxy or phenoxy, one of R$_3$ and R$_4$ is hydrogen and the other is NR$_5$R$_6$, wherein R$_5$ and R$_6$ are each independently selected from hydrogen, C$_{2-8}$alkyl, phenyl, benzyl, or together with the nitrogen to which they are attached, form a saturated or unsaturated 5-7-membered ring.

The thiazide diuretics are a class of compounds which act at a "thiazide receptor", which is believed to be a sodium-chloride symporter. These compounds inhibit Na$^+$Cl$^-$ reabsorption by blocking the thiazide-sensitive Na$^+$Cl$^-$ transporter. The term refers to the chemical structure of the original thiazide diuretics, which contained a thiazide ring system, but the term now encompasses compounds which do not have the thiazide moiety but have a similar action. Because of their vasodilator properties, they are often used to treat hypertension. The skilled person will understand and recognise which compounds are also thiazide diuretics. Examples of thiazide diuretics excluded from the scope of the present invention include: althiazide, bemetizide, benzhydrochlorothiazide, benzthiazide, buthiazide, cyclothiazide, methclothiazide, paraflutizide, polythiazide, teclothiazide, trichloromethazide, chloroaminotenamide, indapamide, chlorthalidone, clofenamide, clorexolone, fenquizone, mefruside, tripamide, clorsulon, clopamide, sulpiride, xipamide, chlorthalidone, cyclopenthiazide, bendroflumethazide, meticrane, quinethazone, chlorthiazide, hydrochlorthiazide, metolazone, cyclopenthiazide, flumethiazide and hydroflumethiazide.

A number of known thiazide diuretics contain an SO$_2$NH$_2$ moiety that further contain one of the residues as depicted below:

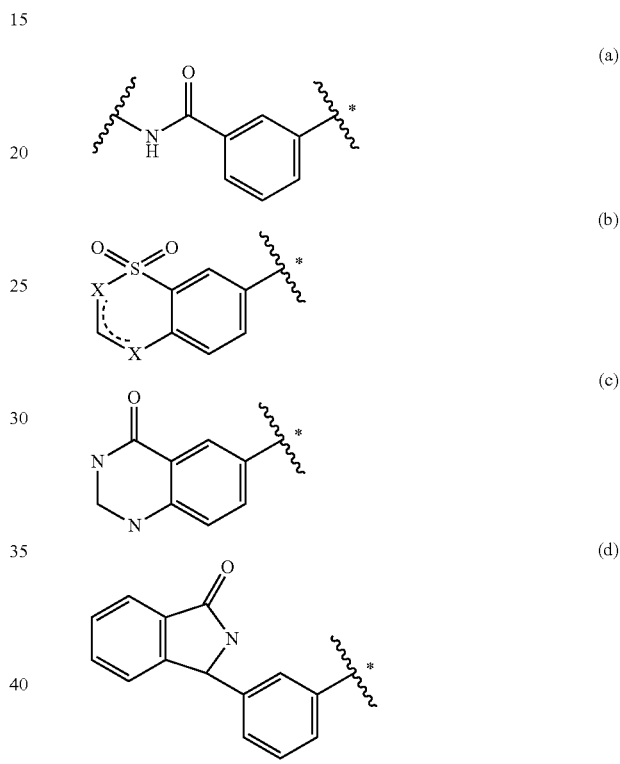

where * is the point of attachment to the sulfonamide group and for (c), where X are both C or both N.

Since both thiazide and loop diuretics inhibit the resorbtion of sodium chloride, through inhibition of the sodium-chloride transporter or the sodium-potassium-dichloride transporter respectively, whereas pure carbonic anhydrase inhibitors inhibit the resorbtion of sodium bicarbonate, not sodium chloride, it is possible to determine the "thiazide" or "loop diuretic" behaviour of a selected carbonic anhydrase inhibitor by the effect of the said carbonic anhydrase inhibitor on chloride excretion. This might be done by way of an analysis of the urine of animals treated with the said carbonic anhydrase inhibitor in comparison with untreated animals using well known methods for the determination of chloride in biological fluids (HPLC: Tsikas, D. et al Chromatographia 1992 33 317; Ion sensitive electrode: Warwick, W. J. et al Clinical Chemistry 1978 24 2050) to determine if there is a significant increase in chloride excretion.

Examples of CAI compounds which may be suitable for use in the present invention are known and extensively described in the literature, such as Pastorekova et al, Journal of Enzyme Inhibition and Medicinal Chemistry, 2004, 19 (3), 199-229, U.S. Pat. No. 2,554,816, U.S. Pat. No. 5,010,204, U.S. Pat. No. 2,783,241, U.S. Pat. No. 3,157,572, GB 795174, U.S. Pat. No. 2,835,702, U.S. Pat. No. 5,378,703, U.S. Pat. No. 5,153,192, U.S. Pat. No. 5,240,923, U.S. Pat. No. 5,679,670 and U.S. Pat. No. 5,585,377.

In a further aspect, the present invention provides a method for determining whether a compound may be suitable for use in the therapeutic applications contemplated herein. Accordingly, the invention also provides a method for selecting a compound for use in accordance with the invention, comprising the steps of:
 (i) selecting a sulfonamide compound or isostere thereof, optionally from the group defined by Formula (I);
 (ii) determining its CA inhibitory activity;
 (iii) determining whether it is a loop diuretic or thiazide diuretic,
wherein a sulfonamide compound or isostere thereof which is a CAI but not also a loop or thiazide diuretic may be suitable for use in accordance with the invention.

Determination of CA inhibitory activity and whether a compound is a loop or thiazide diuretic can be based on knowledge already within the art, or alternatively by an appropriate method, for example a method as described herein.

One class of CAI compounds contemplated by an embodiment of the present invention are compounds wherein the sulfonamide group (or its isostere) is substituted onto an aromatic ring-containing core, e.g. compounds of Formula (I) wherein A is aryl or heteroaryl. In further examples, A is a bicyclic group, such as a 9-10-membered bicyclic aryl, heterocyclyl or heteroaryl group. In other examples, A is a monocyclic 5-6 membered heteroaryl or heterocyclyl group.

Some examples of suitable A include: phenyl, thienyl, pyridinyl, pyrimidnyl, pyrazinyl, pyridazinyl 1,3,5-triazinyl, imidazolidinyl, imidazolinyl pyrrolyl, furyl, imidazolyl, pyrazolyl, thiazolyl, isothiazolyl, 1,2,3-oxidiazolyl, 1,2,4-oxidiazolyl, 1,2,3-triazolyl, 1,2,4-triazolyl, 1,2,4-thiadiazolyl, 1,3,4-thiadiazolyl, 1,3,4-thiadiazolinyl, oxazolyl, isoxazolyl, tetrazolyl, napthyl indanyl, indolyl, isoindolyl, indulinyl, indazolyl, benzimidazolyl, benzothiazolyl, benzisoxazolyl, benzisothiazolyl, quinolinyl, coumarin, isoquinolinyl, cinnolinyl, phthalazinyl, quinazolinyl, quinoxalinyl, pteridinyl, s-triazolo[4,3-a]pyridinyl, theophyllinyl, imidazo[2,1-b]thiazolyl, imidazo[2,1-b]thiophenyl, 1,3,4-thiadiazolo[3,2-a]pyrimidinyl, 1,3,4-thiadiazolo[3,2-a]triazineyl, thieno[2,3-b]thiopyranyl, thieno[3,2-b]thiopyranyl, thieno[2,3-b]pyranyl, thienopiperidinyl, doxanyl, thieno[2,3-b]pyrrolyl, thieno[2,3-b]thiophenyl, thieno[3,2-b]thiophenyl, thieno[2,3-b]furyl, thieno[2,3-b]thiazinyl, 1,3,4-thiadiazolo[2,3-c][1,2,4]thiadiazolyl, imidazo[2,1-b]-1,3,4-thiadiazolyl, benzimidazo[1,2-c][1,2,3]thiadiazolyl, morpholinyl, thiomorpholinyl, piperazinyl pyrazolidinyl, pyrazolinyl, pyrrolidinyl, cyclohexyl, cyclopentyl, and cyclohexyl,
 each of which may be further optionally substituted as described herein.

In further embodiments, A is a 5-membered heterocyclic or heteroaryl group selected from optionally substituted:

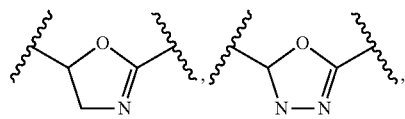

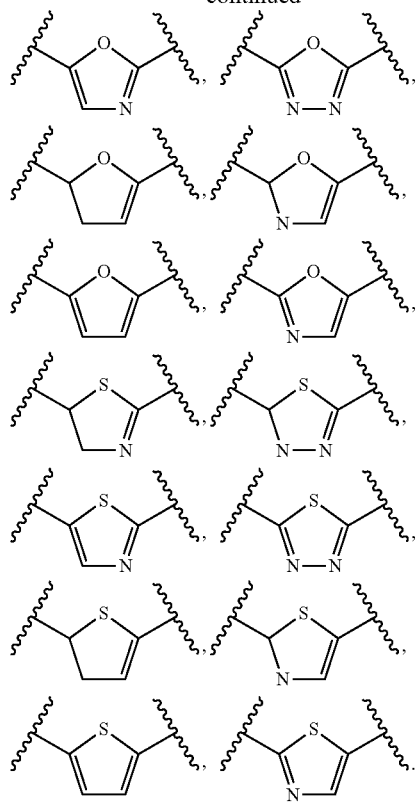

wherein the wavy line on the right handed side of the ring depicts connection to W—X (in further embodiments thereof W is a direct bond between A and X) and the wavy line on the left hand side of the molecule depicts one exemplary site of further substitution (although other sites are possible instead of or as well as that depicted).

In further embodiments, A is linear or branched $C_{2-20}$ alkyl, or $C_{2-20}$ cycloalkyl or a 3-20 membered heterocyclyl group, wherein the cycloalkyl or heterocyclyl group may be monocyclic, bicyclic, or polycyclic (e.g. tricyclic). Advantageously, the A group may be substituted one or more times by an optional substituent as described herein, particularly, halo (e.g. F), hydroxy and methoxy.

In some embodiments of the invention, W is a direct bond. In other embodiments, W is an alkylene chain of 1, 2 or 3 carbon atoms. In yet other embodiments, W is an alkylene chain of 1, 2, 3, 4 or 5 chain atoms, wherein one of the chain atoms is O, S or N(H), provided that the O, S or N atom is not directly attached to X so as to form a —O—O—, —S—O—, —(H)N—O—, O—S—, S—O—, (H)N—O—, —O—N—, or S—N— group (wherein the right hand atom depicted is the atom of the sulfonamide or isostere group).

In some embodiments of the invention, X is selected from the group of: —SONH$_2$, —SO$_2$NHOH, —SO$_2$NHSH, —SO$_2$NHCN, —SO$_2$NHNH$_2$, —SO$_2$NH—1-imidazolyl, —SO$_2$NHPO$_3$H$_2$, —SO$_2$NHSO$_2$NH$_2$, —SO$_2$NHSO$_2$OH, —OSO$_2$NH$_2$—OSO$_2$NHOH, —OSO$_2$NHPO$_3$H$_2$, —OSO$_2$NHSO$_2$NH$_2$, —OSO$_2$NHSO$_2$OH, —NSO$_2$NH$_2$, —NSO$_2$NHOH, —NSO$_2$NHPO$_3$H$_2$, —NSO$_2$NHSO$_2$NH$_2$, —NSO$_2$NHSO$_2$OH, and =NSO$_2$NH$_2$ In further examples, compounds contemplated herein may contain 1, 2 or 3 of the embodiments described above.

Some non-limiting examples of sulfonamide CAIs which are not loop or thiazide diuretics contemplated by the present invention include: acetazolamide, methazolamide, dichlorphenamide, butazolamide, benzolamide, and ethoxzolamide.

Some further examples of CAIs which may be suitable for use in the present invention include those of Formula (II), wherein ===== depicts a single or double bond as defined:

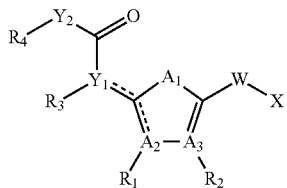

(II)

X is SONH$_2$ or an isostere thereof;
W is a direct bond between A and X, or an alkylene chain of 1 to 5 carbon atoms, wherein a CH$_2$ group may be optionally replaced by O, S or NH;
A$_1$ is selected from S or O;
===== A$_2$ is —CH, =C, =N or —N;
A$_3$ is C or N;
R$_1$ is selected from hydrogen, alkyl, arylalkyl, and aryl when ===== A$_2$ is —N; or is selected from hydrogen, alkyl, carbocyclyl, arylalkyl, aryl, amino, alkoxyalkyl, hydroxy, alkoxy, halo, carbocyclylalkyl, hydroxyalkyl, alkoxy alkoxy, haloalkyl, haloalkoxy and aminoalkyl when ===== A$_2$ is —CH or =C, or is absent when ===== A$_2$ is =N;
R$_2$ is selected from hydrogen, alkyl, carbocyclyl, arylalkyl, aryl, amino, alkoxyalkyl, hydroxy, alkoxy, halo, carbocyclylalkyl, hydroxyalkyl, alkoxy alkoxy, haloalkyl, haloalkoxy and aminoalkyl when A$_3$ is C; or is absent when A$_3$ is N;
Y$_1$ ===== is selected from a direct bond, C=, N=, CH— and N—, provided that when ===== A$_2$ is =C or =N, then Y$_1$ ===== is not C= or N=;
Y$_2$ is selected from NH or CH$_2$;
R$_3$ is selected from hydrogen, alkyl, carbocyclyl, arylalkyl, aryl, amino, alkoxyalkyl, hydroxy, alkoxy, halo, carbocyclylalkyl, hydroxyalkyl, alkoxy alkoxy, haloalkyl, haloalkoxy and aminoalkyl;
or is absent when Y$_1$ ===== is a direct bond; and
R$_4$ is selected from hydrogen, alkyl, arylalkyl and aryl.

The heterocyclic ring of (II) may be aromatic or non-aromatic.

In some embodiments, A$_1$ is O. In other embodiments A$_1$ is S.

In some embodiments, ===== A$_2$ is —CH. In other embodiments, ===== A$_2$ is =C. In yet other embodiments, ===== A$_2$ is —N. In still further embodiments, ===== A$_2$ is =N.

In some embodiments. A$_3$ is C. In other embodiments. A$_3$ is N.

In further embodiments thereof, "alkyl" or "alk" is C$_{1-6}$, "carbocyclyl" is C$_{3-6}$ and "aryl" is phenyl or optionally substituted phenyl.

In still further embodiments, A$_3$ is N, ===== A$_2$ is —N and Y$_1$ ===== is N=.

Other examples of CAIs suitable for use in the present invention include methazolamide and its analogues. Methazolamide and methazolamide analogue CAIs include thiadiazolinyl compounds of Formula (III), and isosteres thereof:

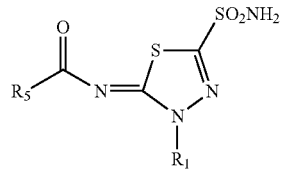

(III)

wherein
R$_1$ is selected from hydrogen, C$_{1-6}$alkyl, C(O)C$_{1-6}$alkyl, and (CH$_2$)$_n$ phenyl, where n is 1, 2, 3, 4, 5 or 6 and phenyl may be optionally substituted by one or more substituents independently selected from C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl; and
R$_5$ is selected from hydrogen, C$_{1-6}$alkyl, C(O)C$_{1-6}$alkyl and (CH$_2$)$_n$ phenyl, where n is 1, 2, 3, 4, 5 or 6 and phenyl may be optionally substituted by one or more substituents independently selected from C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl.

In further embodiments, R$_1$ is C$_{1-6}$alkyl or (CH$_2$)$_n$phenyl and R$_5$ is hydrogen, C$_{1-6}$alkyl or (CH$_2$)$_n$phenyl.

Some particular, non-limiting examples of Formula (III) include:
5-formylimino-4-methyl-Δ$^2$-1,3,4-thiadiazoline-2-sulfonamide,
5-acetylimino-4-methyl-Δ$^2$-1,3,4-thiadiazoline-2-sulfonamide (methazolamide),
5-acetylimino-4-ethyl-Δ$^2$-1,3,4-thiadiazoline-2-sulfonamide,
5-acetylimino-4-butyl-Δ$^2$-1,3,4-thiadiazoline-2-sulfonamide,
5-acetylimino-4-benzyl-Δ$^2$-1,3,4-thiadiazoline-2-sulfonamide,
5-acetylimino-4-p-nitrobenzyl-Δ$^2$-1,3,4-thiadiazoline-2-sulfonamide,
5-propionylimino-4-methyl-Δ$^2$-1,3,4-thiadiazoline-2-sulfonamide,
5-propionylimino-4-ethyl-Δ$^2$-1,3,4-thiadiazoline-2-sulfonamide,
5-propionylimino-4-butyl-Δ$^2$-1,3,4-thiadiazoline-2-sulfonamide,
5-butyrylimino-4-methyl-Δ$^2$-1,3,4-thiadiazoline-2-sulfonamide and
5-butyrylimino-4-benzyl-Δ$^2$-1,3,4-thiadiazoline-2-sulfonamide.

CAI compounds may be obtained from commercial sources or prepared by methods in the patent literature and those well known in the art. For example, the preparation of various heterocyclic sulfonamides, including acetazolamide and related compounds, is described in U.S. Pat. No. 2,554,816 and U.S. Pat. No. 5,010,204. The preparation of various thiazoles, 1,3,4-thiadiazoles, and 1,3,4-thiadiazolines including methazolamide and other 5-acylimino-4-substituted-Δ$^2$-1,3,4-thiadiazoline-2-sulfonamides, is described in EP 96003, Recueil des Travaux Chimiques des Pays-Bas et de la Belgique (1943), 62, 207-09, U.S. Pat. No. 2,978,457, U.S. Pat. No. 2,994,701, Angewandte Chemie, (1966), 78(18-19), 850-5, WO 2002012211, WO 9529904. U.S. Pat. No. 2,783,241 and U.S. Pat. No. 3,157,572. The preparation of various heterocyclic sulfonamides, such as ethoxolamide and analogues, is described in GB 795174.

Certain compounds of Formula (I)-(II) may also exist in tautomeric form, (e.g. keto-enol tautomers). All such forms are also contemplated herein.

The compounds and compositions contemplated by the invention may be administered as the sole insulin sensitising agent, e.g. anti-diabetic therapeutic agent or as a combination in conjunction with insulin (human, bovine, porcine or synthetic) and/or one or more other anti-diabetic or anti-hyperglycaemic therapeutic agents and may be administered, simultaneously (separately or as a combination/composition) or sequentially in accordance with a suitable dosing and treatment regime as can be determined by the attending physician. Suitable other agents may include insulin sensitisers, insulin secretagogues glucose resorption/uptake inhibitors and the classes and compounds identified in US2005/0037981, particularly Table 2, the contents of which are incorporated herein in their entirety. Some examples of agents for use in conjunction with the invention include biguanides, sulfonylureas, meglitinides, insulin and insulin analogues, and thiazolidinediones. Exemplary such agents contemplated, but are not limited to, include thiazolidinediones (including rosiglitazone and pioglitazone), metformin, insulin, sulphonylureas (including glimepiride, glyburide, glipizide, chlorpropamide, tolazamide and tolbutamide), meglitimides (including repaglinide and nateglinide), a-glucosidase inhibitors (including a carbose and miglitol), DPPIV inhibitors such as sitagliptin. Particular combinations include such agents together with a compound of Formula (I)-(III) as described herein.

In embodiments of the invention, the compounds contemplated by the invention may be administered to a subject who is selected for the therapy on the basis of requiring blood glucose regulating treatment by the compounds. Thus, in further embodiments, the methods of the invention are preceded by the step of selecting the subject or patient on the basis of requiring blood glucose regulation, or treatment for diabetes or other condition in which insulin resistance is a factor.

In some embodiments, by administering a sulfonamide (or isostere) CAI according to the invention in combination with another anti-diabetic or anti-hyperglycaemic therapeutic agent, it may be possible to administer reduced dosages of one or both of the agents compared to current monotherapies, i.e. in some embodiments, the combinations may advantageously provide an additive or synergistic effect. Thus, for example, it may be possible to achieve effective therapy by administration of currently used anti-diabetic or anti-hyperglycaemic agent, such as metformin or insulin secretagogues, at a reduced dosage rate than currently clinically used. This may advantageously avoid, ameliorate, or otherwise reduce the severity, risk or occurrence of undesirable side effects and disadvantages associated with currently employed dosage amounts and regimes.

In an alternative embodiment, by administering a sulfonamide or isostere CAI according to the invention in combination with another anti-diabetic or anti-hyperglycaemic therapeutic agent, it may be possible to increase the time period for which each of the agents provides a benefit when compared to the period that each agent provides a benefit when used as a monotherapy. Thus, for example, it may be possible to achieve effective therapy for a greater number of months or even years by administration of currently used anti-diabetic or anti-hyperglycaemic agents such as metformin or insulin secretagogues, than is currently achieved. This may advantageously avoid, ameliorate or otherwise reduce the severity, risk or occurance of side effects and other disadvantages associated with the term of therapeutic benefit provided by current treatment regimes.

It has further thus been surprisingly discovered that the combination of metformin with methazolamide, a drug currently used in the treatment of glaucoma, generally at a dosage of 5-150 mg/dose 2-3 times daily, provides an improvement in fasting plasma glucose levels compared to that achieved by metformin alone.

Thus, in some embodiments of the invention, this may advantageously allow for the administration of reduced dosages of metformin compared to current dosage regimes and may thereby overcome, diminish or ameliorate one or more of the disadvantages associated with current metformin therapies.

Thus, a further embodiment of the invention provides a method of lowering blood glucose levels in a subject in need thereof comprising the administration of a combination of metformin, or a pharmaceutically acceptable salt thereof, and a compound of Formula (IT) or a pharmaceutically acceptable salt thereof.

Another embodiment provides a method of treating insulin resistance in a subject in need thereof comprising the administration of a combination of metformin, or a pharmaceutically acceptable salt thereof, and a compound of Formula (II) or a pharmaceutically acceptable salt thereof.

Yet another embodiment of the invention relates to a method for treating a disease or condition, or symptom thereof, in which insulin resistance is involved, comprising the administration of a combination of metformin, or a pharmaceutically acceptable salt thereof, and a compound of Formula (IT) or a pharmaceutically acceptable salt thereof.

In certain embodiments, the compound of Formula (II) is methazolamide. In further embodiments, the combination comprises metformin hydrochloride and methazolamide.

In one or more embodiments of the invention, the compounds or combinations contemplated by the invention may provide short term alleviation or relief of one of more symptoms of diabetes and related or precursor conditions, such as elevated blood glucose levels. In further embodiments, treatment in accordance with the invention may provide a measurable or noticeable alleviation, improvement or relief within about 30 minutes to about 12 hours and up to about 7 days from initiation of treatment. In still further embodiments, treatment in accordance with the invention may provide a measurable or noticeable alleviation or relief within 1 hour to up to 4 days, typically within about 24 hours to 4 days.

As used herein, the terms "regulate" or "modulate" and variations such as regulating/modulating and regulation/modulation, when used in reference to glucose homeostasis, refer to the adjustment or control of said glucose levels, in particular embodiments, the adjustment to or maintenance of normal blood glucose levels. Thus, "regulating/modulating glucose homeostasis" includes the adjustment or control of blood glucose levels to lower hyperglycaemic, or advantageously achieve or maintain normal fasting state, blood glucose levels. Normal fasting state blood glucose levels are typically less than 6.1 mmolL$^{-1}$ (110 mgdL$^{-1}$). Hyperglycaemic levels (also referred to herein as elevated blood glucose levels) refer to fasting blood glucose levels greater than or equal to 6.1 mmolL$^{-1}$ (110 mgdL$^{-1}$).

Impaired fasting glycemia (IFG) is characterised by a fasting plasma glucose concentration greater than or equal to 6.1 mmolL$^{-1}$ (110 mgdL$^{-1}$) but less than 7.0 (126 mgdL$^{-1}$) and a 2-h plasma glucose concentration during the oral glucose tolerance test (OGTT) (if measured) less than 7.8 mmolL$^{-1}$ (140 mgdL$^{-1}$). Impaired glucose tolerance (IGT) is characterised by a fasting plasma glucose concentration of less than 7.0 mmolL$^{-1}$ (126 mgdL$^{-1}$) and a 2-h plasma glucose concentration during the OGTT of greater than or equal to 7.8 mmolL$^{-1}$ (140 mgdL$^{-1}$) but less than 11.1 mmolL$^{-1}$ (200 mgdL$^{-1}$). Diabetes is characterised by a fasting plasma glucose concentration of greater than or equal to 7.0 mmolL$^{-1}$ (126 mgdL$^{-1}$) or a 2-h plasma glucose concentration during the OGTT of greater than 11.1 mmolL$^{-1}$ (200 mgdL$^{-1}$).

The compounds and combinations contemplated by the invention may have utility as insulin sensitisers in the therapeutic or prophylactic treatment of diseases and associated conditions, and/or one or more of their symptoms, in a subject, in which insulin resistance in involved or implicated. Any disease or condition, or symptom thereof in which insulin resistance or impaired glucose uptake by a cell or tissue can be attributed, or play a role or is manifested is contemplated herein. Non-limiting examples include NIDDM, gestational diabetes, impaired glucose tolerance, impaired fasting glucose, Syndrome X, hyperglycemia, atheriosclerosis, hypertriglyceridemia, dyslipidemia, hyperinsulinemia, nephropathy, neuropathy, ischemia, stroke and fatty liver disease. Typically, the disease or condition is NIDDM, gestational diabetes, impaired glucose tolerance, impaired fasting glucose, Syndrome X or hyperglycemia. Agents for the treatment of associated conditions, such as cardiovascular disease (e.g. antihypertensive agents), may also be administered in conjunction (together with or separately) with the invention. It will be understood that a subject may not necessarily suffer from or develop all symptoms or associated conditions in which insulin resistance is involved or implicated, or, they may not be severe enough to warrant additional therapeutic treatment particularly if the disease or condition is detected and treated at an early stage. For example, in certain embodiments of the invention, the subject having elevated blood glucose levels may not be suffering from other symptoms or associated conditions, such as cardiac or cardiovascular conditions associated with, for example, diabetes due to insulin resistance. Alternatively, such associated symptoms or conditions, if manifested, may not be in need of conjunctive therapeutic treatment therefor. Alternatively, any such associated symptoms or conditions may be treated with an appropriate agent, e.g. anti-hypertensives such as diuretics, ACE inhibitors or beta-blockers as determined by the attending physician.

Subjects to be treated include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention. A particularly contemplated subject is a human subject.

The compounds of the invention are administered in an amount which, when administered according to the desired dosing regimen, attains, or at least partially attains, the desired therapeutic effect, e.g. modulating glucose homeostasis, modulating cellular glucose uptake, treating insulin resistance, lowering blood glucose levels or treating a disease or condition, or symptom thereof, in which insulin resistance is involved. As used herein, treatment refers to therapeutic ameliorating treatment or prophylactic treatment, and may include one or more of: alleviating or ameliorating the symptoms of, preventing or delaying the onset of, inhibiting the progression of, or halting or reversing altogether the onset or progression of the particular disorder or condition, or one or more symptoms thereof, being treated.

Suitable dosage amounts and dosing regimens can be determined by the attending physician and may depend on the particular condition being treated, the severity of the condition as well as the general age, health and weight of the subject, and may be in the range of from about 0.01 mg to about 1000 mg of active per day, such as from about 0.05 mg to about 500 mg, or from about 0.1 to 250 mg of active per day. The active ingredient may be administered in a single dose or a series of doses. Suitable dosages may contain about 0.25, 0.5, 1.0, 2.5, 5.0, 10, 20, 25, 50, 75, 100, 150, 200, 250 or 500 mg of active. In certain embodiments, relatively low doses of the compounds contemplated herein may be used to achieve the desired effect. Advantageously, the compounds may be administered in a dosage of between 0.001 to 10 mg/kg/day, such as 0.01 to 5 mg/kg/day or 0.25 to 2.5 mg/kg/day. In certain embodiments of the invention, the compounds are administered once a day, as a single dose, or a divided dose twice a day.

As described above, combinations according to the invention using metformin, or a pharmaceutically acceptable salt thereof, may advantageously allow for reduced dosage amounts of metformin (or pharmaceutically acceptable salt) compared to known metformin therapies, particularly metformin monotherapy. In some embodiments, the dosage amounts of the combinations are such that they may provide an additive or synergistic effect. Suitable dosage amounts and dosing regimens can be determined by the attending physician and may depend on the particular condition being treated, the severity of the condition as well as the general age, health and weight of the subject.

In some embodiments of the invention, the daily dosage amount of metformin (or pharmaceutically acceptable salt) administered in the combination is equal to or less than about 90% of that which would be required for metformin monotherapy. In further embodiments, the dosage is equal to or less than about 80/o, 70%, 60% or 50% of that which would be required for metformin monotherapy. Exemplary daily dosage amounts of metformin for an adult may be in the range of from about 100 mg to about 1500 or 2000 mg of active per day, such as about 250 mg, 500 mg, 750 mg, 850 mg, 1000 mg, 1100 or 1250 mg. Exemplary daily dosage amounts for pediatric patients (10-16 years) may be in the range from about 50, to about 1000 mg or 1500 mg per day, such as about 100 mg, 250 mg, 500 mg, 750 mg, 850 mg, 1100 mg or 1250 mg per day. The active ingredient may be administered in a single dose or a series of doses. Suitable dosages forms may contain about 50, 75, 100, 150, 200, 250, 500 750, 850 or 1000 mg of metformin active.

Suitable daily dosage amount of methazolamide (or analogue) administered in the combinations of the invention may fall in the range of about 10 mg to about 300 per day, such as 25 mg, 50 mg, 75 mg, 100 mg, 125 mg, 150 mg or 250 mg.

In certain embodiments of the invention, the administration of a combination according to the invention may advantageously achieve effective therapy for a period of months (for example 3-36 months) or years (for example 1-10 years) compared to the corresponding anti-diabetic or anti-hyperglycaemic monotherapy.

While it is possible for the CAI compound to be administered alone, it is preferable to present it as a composition, preferably as a pharmaceutical composition, with one or more pharmaceutically acceptable adjuvants. Thus, the present invention also relates to the use of a carbonic anhydrase inhibitor compounds contemplated herein, or a pharmaceutically acceptable salt, solvate or prodrug thereof, in the manufacture of a medicament for modulating glucose homeostasis, modulating cellular glucose uptake, treating insulin resistance, or lowering blood glucose levels.

The formulation of such compositions is well known to those skilled in the art, see for example, *Remington's Pharmaceutical Sciences*, 18th Edition, Mack Publishing, 1990. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, inhalable, nasal, topical (including dermal, buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, appropriate coatings, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The present invention also relates to prodrugs CAI compounds. Any compound that is a prodrug of a CAI compound is within the scope and spirit of the invention. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as an acetate, or thioester or where a free amino group is converted into an amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters include $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.*, 1979, 20, 369, Kyncl, J. et al), enamines (see, for example, *J. Pharm. Sci.*, 1971, 60, 1810, Caldwell, H. et al), Schiff bases (see, for example, U.S. Pat. No. 2,923,661 and *Antimicrob. Agents Chemother.*, 1981, 19, 1004, Smyth, R. et al), oxazolidines (see, for example, *J. Pharm. Sci*, 1983, 72, 1294. Johansen, M. et al), Mannich bases (see, for example, *J. Pharm. Sci.* 1980, 69, 44, Bundgaard, H. et al and *J. Am. Chem. Soc.*, 1959, 81, 1198, Gottstein, W. et al), hydroxymethyl derivatives (see, for example, *J. Pharm. Sci*, 1981, 70, 855, Bansal, P. et al) and N-(acyloxy)alkyl derivatives and carbamates (see, for example, *J. Med. Chem.*, 1980, 23, 469, Bodor, N. et al, *J. Med. Chem.*, 1984, 27, 1037, Firestone, R. et al, *J. Med. Chem.*, 1967, 10, 960, Kreiger, M. et al, U.S. Pat. No. 5,684,018 and *J. Med. Chem.*, 1988, 31, 318-322, Alexander, J. et al). Other conventional procedures for the selection and preparation of suitable prodrugs are known in the art and are described, for example, in WO 00/23419; *Design of Prodrugs*, H. Bundgaard, Ed., Elsevier Science Publishers, 1985; *Methods in Enzymology*, 42: 309-396, K. Widder, Ed, Academic Press, 1985; *A Textbook of Drug Design and Development*, Krogsgaard-Larsen and H. Bundgaard, Eds, Chapter 5, p113-191 (1991); *Advanced Drug Delivery Reviews*, 8; 1-38 (1992); *Journal of Pharmaceutical Sciences*, 77; 285 (1988), H. Bundgaard, et al; *Chem Pharm Bull*, 32692 (1984), N. Kakeya et al and *The Organic Chemistry of Drug Desig and Drug Action*, Chapter 8, pp 352-401, Academic press, Inc., 1992.

Suitable pharmaceutically acceptable salts of compounds of formula (I) include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, 0-(p-hydroxybenzoyl)benzoic, 4'-4"-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

The compounds of the invention may be in crystalline form either as the free compounds or as solvates and it is intended that both forms are within the scope of the present invention. The term "solvate" refers to a complex or aggregate formed by one or more molecules of a solute, i.e. compounds contemplated by the invention, and one or more molecules of a solvent. Suitable solvents are well understood in the art and include for example, of water, i.e. to form hydrates, and common organic solvents such as alcohols (methanol, ethanol, isopropanol) and acetic acid. Methods of solvation are generally known within the art.

The compounds of the invention may also be presented for use in veterinary compositions. These may be prepared by any suitable means known in the art. Examples of such compositions include those adapted for:

(a) oral administration, external application (e.g. drenches including aqueous and non-aqueous solutions or suspensions), tablets, boluses, powders, granules, pellets for admixture with feedstuffs, pastes for application to the tongue;

(b) parenteral administration, e.g. subcutaneous, intramuscular or intravenous injection as a sterile solution or suspension;

(c) topical application e.g. creams, ointments, gels, lotions etc.

The invention will now be described with reference to the following examples which are provided for the purpose of illustrating certain embodiments of the invention and are not to be construed as limiting the generality hereinbefore described.

EXAMPLES

Example 1. Effect of Dichlorphenamide on Glucose Uptake in 3T3-L1 Adipocytes 3T3-L1 adipoctyes (non-infected) in 96-well plate format were serum-starved overnight (16 to 18 hr) in DMEM containing 0.2% BSA and were untreated or treated with dichlorphenamide at a concentration of 10M. Dichlorphenamide was added during serum-starvation. Cells were then washed twice in Dulbecco's PBS, pH 7.4 (Gibco) containing 0.2% (w/v) RIA-grade BSA, 0.5 mM $MgCl_2$ and 0.5 mM $CaCl_2$. Insulin at 0, 0.5 and 10 nM was added for 20 min at 37° C. Uptake of 50 µM 2-deoxy glucose and 0.5 µCi 2-deoxy-[U-$^3$H] glucose (NEN, PerkinElmer Life Sciences) per well was measured over the final 10 min of insulin stimulation. The reaction was stopped upon addition of ice-cold 80 µg/ml phloretin in PBS, pH 7.4 and cells were solublised in 0.03% (w/v) SDS. Counts per minute (cpm) were measured by scintillator counter. These results are presented below in Table 1-1.

The data in Table 1-1 shows that dichlorphenamide enhanced basal 2-deoxyglucose uptake as well as sub-maximal (0.5 nM) and maximal (10 nM) insulin stimulated 2-deoxyglucose uptake (results represent the mean of three independent experiments) and each experiment was assayed in quadruplicate. The data is expressed as a mean±SEM. The statistical analysis was performed using an umpaired t-test (2-tailed).

TABLE 1-1

Effect of Dichlorphenamide (DCP) on 2-Deoxyglucose Uptake by 3T3-L1 adipocytes

| 2-Deoxyglucose uptake (Normalised: Vehicle with no insulin = 100%) | Untreated | Treated DCP 10 µM |
|---|---|---|
| Vehicle | 100 ± 12 | 508 ± 57[1] |
| 0.5 nM Insulin | 749 ± 66 | 1468 ± 400[2] |
| 10 nM Insulin | 2063 ± 205 | 1826 ± 97 |

[1] p = 0.02;
[2] p = 0.05

Example 2. Effect of Dichlorphenamide on Glucose Tolerance in Obese *Psammomys obesus* (Israeli Sand Rats)

The outbred Israeli sand rat, *Psammomys obesus* is a unique animal model for the study of obesity and diabetes. When housed under standard laboratory conditions, a proportion of Israeli sand rats become obese and develop type 2 diabetes spontaneously, without requiring high caloric feeding like the diet-induced obese mouse model, or as a consequence of a mutation in a particular gene as in the db/db mouse model. In this regard their evolution into a diabetic state closely resembles the environmental and polygenic human condition. Type 2 diabetic *P. obesus* are also profoundly insulin resistant, as measured by the area under the blood glucose curve during an oral glucose tolerance test (OGTT). In addition, a proportion of the animals remain lean and healthy under these same conditions, while others develop a range of intermediate phenotypes. This response is similar to that seen in human populations.

Diabetic *P. obesus* are characterised by having elevated blood glucose levels. Animals which have blood glucose of >8.0 mM are considered diabetic (Barnett et al., *Diabetologia* 1994; 37:671-676), and the magnitude of the reduction in blood glucose, as well as reduction in the area of the OGTT plasma glucose curve following treatment with a compound are taken as a measure of the efficacy of that compound in improving the animal's glucose metabolism.

16 Week old obese normoglycaemic and hyperinsulinemic male *P. obesus* (Walder et al, *Int J Exp Diabetes Res.* 2000:1(3):177-84; and Trevaskis et al, *Comp Biochem Physiol B Biochem Mol Biol.* 2004 137(1):65-73) were starved for 4 hours before the administration of 20 mg/Kg Dichlorphenamide in saline by oral gavage (5 ml per gram of body weight) using feeding tubes (41×0.17 cm, Kendall Co., Mansfield, Mass. USA). After another 4 hours glucose (2 g/Kg of body weight) was administered to the animals by oral gavage. 50 ml blood samples were taken from the tail at each time point; 0, 15, 30, 45, 60 and 90 minutes after the glucose delivery to determine blood glucose and insulin levels. Glucose was measured in whole blood using a YSI glucose analyser (Model #2300 STAT PLUS, Yellow Springs Instruments Co., Ohio, USA). The instrument takes a sample aliquot of 25 μl and is calibrated every 10 samples using 5.55 and 8.33 mmol/L glucose standards. The analyser utilises a probe fitted with a 3-layer membrane containing an immobilised enzyme. J3-D-glucose is oxidised by glucose oxidase, which is immobilised on a polycarbonate cellulose membrane, to form glucono-( )-lactone and hydrogen peroxide. The hydrogen peroxide in turn, is oxidised at the platinum anode, producing electrons. The electron flow is linearly proportional to the steady state hydrogen peroxide concentration and therefore to the concentration of glucose in the sample. Insulin levels were measured in plasma obtained after the clotting of a blood sample in heparin-coated tubes. Plasma insulin concentrations were determined using a commercially-available double antibody radio-immunoassay (RIA) kit. (Linco Research Inc., USA). Plasma insulin samples were measured by the competition of insulin with 125-iodine-labelled insulin for binding sites on highly specific antibodies. In the procedure, 20 μl of plasma sample (in duplicate) was added to 50 μl of 125-iodine-labelled insulin (tracer) and 50 μl of guinea pig anti-insulin antibody (first antibody). Solutions were then incubated for 2 hours before adding 1 ml of sheep anti-guinea pig antibody (second antibody) and left to incubate again for 30 min at room temperature. Bound and free insulin were then separated by centrifugation at 3,500 g for 20 min (Beckman Centrifuge Model J6B, Beckman Instruments, Gladesville, Australia), leaving the bound insulin in a pellet at the bottom of the tube following aspiration of each sample. A gamma counter (Minaxi g Auto-gamma 5000 series, Packard Instrument Company, IL, USA) with a counting time of 1 min was then used to measure the radioactivity of the solid phase pellet. The results are presented in Table 2-1.

The data in Table 2-1 showed that treatment with Dichlorphenamide increased the glucose tolerance of diabetic *P. obesus* as measured by a reduction in the area under the plasma glucose curve and the plasma insulin curve in an oral glucose tolerance test.

TABLE 2-1

Effect of dichlorphenamide on glucose tolerance in obese *Psammomys obesus*

| Time (min) after glucose gavage | Plasma Glucose (mM) | | Plasma Insulin (mU/ml) | |
|---|---|---|---|---|
| | Vehicle | 20 mg/Kg DCP | Vehicle | 20 mg/Kg DCP |
| 0 | 3.5 ± 0.1 | 3.4 ± 0.2 | 48 ± 10 | 48 ± 15 |
| 15 | 5.5 ± 0.6 | 5.4 ± 0.2 | 290 ± 69 | 141 ± 21 |
| 30 | 6.3 ± 0.4 | 4.7 ± 0.4* | 263 ± 68 | 149 ± 49 |
| 45 | 6.9 ± 0.4 | 5.1 ± 0.3* | 161 ± 34 | 123 ± 39 |
| 60 | 6.6 ± 0.5 | 4.7 ± 0.4* | 217 ± 57 | 202 ± 46 |
| 90 | 5.4 ± 0.5 | 4.3 ± 0.4 | 160 ± 45 | 117 ± 22 |
| AUC (mM · min) | 218 ± 32 | 119 ± 16* | 14,014 ± 3075 | 8,548 ± 2441 |

Data represent the mean ± SE of 6 animals per group.
*$p < 0.02$

Example 3. Effect of Dichlorphenamide on Fasting Blood Glucose Levels in Diet-Induced Obese (DIO) Mice (*Mus Musculus*)

Mice of the strain C57BL/6J fed with a commercially available high fat diet (45% fat) for 10 weeks develop obesity (body fat>20% body weight), mild hyperglycaemia (plasma glucose concentrations of 8-10 mM), and glucose intolerance (area under the plasma glucose curve of an intraperitoneal glucose tolerance test of >1200 mM·min). This animal model, the Diet-induced obese mouse model, (DIO) is extremely useful for studying insulin resistance in a pre-diabetic state with a strong environmental component. Insulin resistance in this model is characterised by an increase in the area under the blood glucose curve following an intraperitoneal injection of glucose (IPGTT), and the magnitude of the reduction in the area of this blood glucose curve following treatment with a compound is taken as a measure of the efficacy of that compound in improving the animal's glucose metabolism.

Compound Preparation and Administration
Dosing Solutions of the Test Articles:

Dichlorphenamide dosing solutions were prepared fresh on each dosing day and stored at room temperature, protected from light. The compound was formulated in sterile saline.

Animals

Male C57Bl/6J mice were obtained at 8 weeks of age from Animal Resources Centre (Canning Vale, Western Australia). Animals were individually housed and allowed free movement and ad libitum access to water and food. Animals were maintained on a 12 hour light (6 am-6 pm)

and 12 hour dark (6 pm-6 am) cycle. Animals were monitored daily. Body weight, food and water intake were recorded 3 times a week. After two weeks acclimatizing, mice were fed a high fat rich diet (SF04-001, Specialty feeds, Glen Forrest, Wash., Australia with a total energy density of 4.7 kcal/g. Caloric distribution in the diet was 20% from protein, 35% from carbohydrates, and 45% from fat) for 14 weeks.

Treatment

During the last two weeks animals in groups of 6 were treated with vehicle or Dichlorphenamide 20 mg/kg in vehicle by oral gavage (5 µl per gram of body weight) using feeding tubes 18 ga (1.2 mm)*38 mm from Instech Solomon (Plymouth, USA).

Fasting Plasma Glucose (FPG) Concentration

The fasting plasma glucose levels of the animals was tested prior to commencement of the study and on day 14 of dosing. The animals were fasted for a period of 4 hours after dosing and prior to the taking of a blood sample via a tail nick. Blood glucose levels were monitored using commercially available glucometers (Accuchek Advantage, Roche) based on the electric current generated when a blood drop is spotted on a test strip resulting in conversion of the glucose present in the sample to gluconolactone by the glucose dehydrogenase enzyme, in the presence of the coenzyme (PQQ). The results are presented in Table 3-1.

The data in Table 3-1 shows that treatment with Dichlorphenamide reduced the fasting plasma glucose levels of diet-induced obese mice.

TABLE 3-1

Effect of dichlorphenamide on fasting blood glucose levels in diet-induced obese mice

| Treatment | FPG Day -1 (mM) | FPG Day 14 (mM) | Delta FPG Treatment Day 14 vs Day -1 | Delta FPG Treatment vs Vehicle Day 14 |
|---|---|---|---|---|
| Vehicle | 10.5 ± 0.4 | 9.33 ± 0.2 | -11% | 0% |
| 20 mg/kg | 10.05 ± 0.2 | 8.35 ± 0.2 | -17%[1] | -11%[2] |

[1]p = 0.002 paired ttest;
[2]p = 0.005 unpaired ttest
Data represent the mean ± SE of 5-6 animals per group.

Example 4. Effect of Dichlorphenamide on Fasting Blood Glucose Levels in Diet-Induced Obese (DIO) Mice (*Mus Musculus*)

Compound Preparation and Administration
Dosing Solutions of the Test Articles:

Dichlorphenamide dosing solutions were prepared fresh on each dosing day and stored at room temperature, protected from light. The compound was formulated in sterile saline.

Animals

Male C57Bl/6J mice were treated as for Example 3.

Treatment

During the last three weeks animals in groups of 6 were treated with vehicle or Dichlorphenamide 20 mg/kg or 50 mg/kg in vehicle by oral gavage (5 µl per gram of body weight) using feeding tubes 18 ga (1.2 mm)*38 mm from Instech Solomon (Plymouth, USA).

Fasting Plasma Glucose (FPG) Concentration

The fasting plasma glucose levels of the animals was tested prior to commencement of the study and on day 19 of dosing. The animals were fasted for a period of 4 hours after dosing and prior to the taking of a blood sample via a tail nick. Blood glucose levels were monitored using commercially available glucometers (Accuchek Advantage, Roche) based on the electric current generated when a blood drop is spotted on a test strip resulting in conversion of the glucose present in the sample to gluconolactone by the glucose dehydrogenase enzyme, in the presence of the coenzyme (PQQ). The results are presented in Table 4-1.

The data in Table 4-1 shows that treatment with Dichlorphenamide improves the glucose tolerance of diet-induced obese mice

TABLE 4-1 ipGTT following Dichlorphenamide treatment in DIO mice

| Treatment | AUC Day -1 | AUC Day 19 | Delta AUC Day 19 vs Day -1 | AUC Day 19 Treat vs Veh |
|---|---|---|---|---|
| Vehicle | 1351 ± 80 | 987 ± 88 | -27%[1] | 0% |
| 20 mg/kg | 1350 ± 56 | 832 ± 80 | -38%[2] | -16% |
| 50 mg/kg | 1345 ± 73 | 908 ± 38 | -32%[1] | -8% |

Data represent the mean ± SE of 5-6 animals per group;
[1]p < 0.01;
[2]p < 0.001

Example 5. Effect of Methazolamide on Fasting Blood Glucose Levels in Diet-Induced Obese Mice (*Mus Musculus*)

Compound Preparation and Administration
Dosing Solutions of the Test Articles:

Methazolamide dosing solutions were prepared fresh on each dosing day and stored at room temperature, protected from light. The compound was formulated in sterile vehicle: Saline:PEG400 65:35 v/v.

Animals

Male C57Bl/6J mice were obtained at 8 weeks of age from Animal Resources Centre (Canning Vale, Western Australia). Animals were individually housed and allowed free movement and ad libitum access to water and food. Animals were maintained on a 12 hour light (6 am-6 pm) and 12 hour dark (6 pm-6 am) cycle. Animals were monitored daily. Body weight, food and water intake were recorded 3 times a week. After two weeks acclimatizing, mice were fed a high fat rich diet (SF04-001, Specialty feeds, Glen Forrest, Wash., Australia with a total energy density of 4.7 kcal/g. Caloric distribution in the diet was 20% from protein, 35% from carbohydrates, and 45% from fat) for 12 weeks.

Treatment

During the last two weeks animals in groups of 6 were treated with doses selected from: vehicle, Methazolamide 10 mg/kg, 20 mg/kg, 50 mg/kg, 100 mg/kg in vehicle by oral gavage (5 µl per gram of body weight) using feeding tubes 18 ga (1.2 mm)*38 mm from Instech Solomon (Plymouth, USA).

Fasting Plasma Glucose (FPG) Concentration

The fasting plasma glucose levels of the animals was tested prior to commencement of the study and on day 13 of dosing. The animals were fasted for a period of 4 hours after dosing and prior to the taking of a blood sample via a tail nick. Blood glucose levels were monitored using commercially available glucometers (Accuchek Advantage, Roche) based on the electric current generated when a blood drop is spotted on a test strip resulting in conversion of the glucose present in the sample to gluconolactone by the glucose dehydrogenase enzyme, in the presence of the coenzyme (PQQ). The results are presented in Table 5-1 and Table 5-2.

The data in Table 5-1 showed that treatment with Methazolamide reduced the fasting plasma glucose levels of diet-induced obese mice.

The date in Table 5-2 showed that treatment with Methazolamide increased the glucose tolerance of diet-induced obese mice.

Body Weight

There was no difference in body weight between any of the treated groups at either Day 0 or Day 13, indicating that the effects of Methazolamide on glucose metabolism were not secondary to changes in body weight.

TABLE 5-1

Fasting plasma glucose during Methazolamide treatment in DIO mice

| Treatment | FPG Day −1 (mM) | FPG Day 13 (mM) | Delta FPG Treatment Day 13 vs Day −1 | FPG Treatment vs Vehicle Day 13 |
|---|---|---|---|---|
| Vehicle | 7.6 ± 0.46 | 7.67 ± 0.34 | 1% | 0% |
| 10 mg/kg | 6.92 ± 0.55 | 7.75 ± 0.43 | 12% | 1% |
| 20 mg/kg | 7.28 ± 0.47 | 6.90 ± 0.24 | −5% | −10% |
| 50 mg/kg | 7.20 ± 0.71 | 6.28 ± 0.31 | −13% | −18%[1] |
| 100 mg/kg | 7.63 ± 0.55 | 6.05 ± 0.15 | −21% | −21%[2] |

[1] p = 0.01;
[2] p = 0.001
Data represent the mean ± SE of 5-6 animals per group.

TABLE 5-2 ipGTT following Methazolamide treatment in DIO mice

| Treatment | AUC Day −1 (mM · min) | AUC Day 13 (mM · min) | Delta AUC Treatment Day 13 vs Day −1 | Delta AUC Treatment vs Vehicle Day 13 |
|---|---|---|---|---|
| Vehicle | 1078 ± 112 | 976 ± 83 | −10% | 0% |
| 10 mg/kg | 1038 ± 129 | 901 ± 139 | −13% | −8% |
| 20 mg/kg | 1070 ± 77 | 619 ± 106 | −42%[1] | −37%[1] |
| 50 mg/kg | 1073 ± 112 | 710 ± 87 | −34%[1] | −27%[1] |
| 100 mg/kg | 1080 ± 59 | 691 ± 60 | −36%[2] | −29%[1] |

Data represent the mean ± SE of 5-6 animals per group;
[1] p ≤ 0.05;
[2] p = 0.005

Example 6. Effect of Chlorthalidone on Fasting Blood Glucose Levels in Diet-Induced Obese Mice (*Mus Musculus*)

Compound Preparation and Administration
Dosing Solutions of the Test Articles:

Chlorthalidone dosing solutions were prepared fresh on each dosing day and stored at room temperature, protected from light. The compound was formulated in sterile vehicle: Saline:PEG400 1:1 v/v.

Animals

Male C57Bl/6J mice were treated as for Example 5.

Treatment

During the last two weeks animals in groups of 6 were treated with doses selected from: vehicle, Chlorthalidone 10 mg/kg, 20 mg/kg and 50 mg/kg in vehicle by oral gavage (5 µl per gram of body weight) using feeding tubes 18 ga (1.2 mm)*38 mm from nstech Solomon (Plymouth, USA).

Fasting Plasma Glucose (FPG) Concentration

The fasting plasma glucose levels of the animals was tested prior to commencement of the study and on day 13 of dosing as for Example 5. The results are presented in Table 6-1 and Table 6-2 and indicate that chlorthalidone has no beneficial effect on fasting plasma glucose or glucose tolerance.

TABLE 6-1

Fasting plasma glucose during Chlorthalidone treatment in DIO mice

| Treatment | FPG Day −1 (mM) | FPG Day 13 (mM) | Delta FPG Treatment Day 13 vs Day −1 | FPG Treatment vs Vehicle Day 13 |
|---|---|---|---|---|
| Vehicle | 7.82 ± 0.61 | 7.7 ± 0.29 | −2% | 0% |
| 10 mg/kg | 7.8 ± 0.31 | 8.08 ± 0.35 | 4% | 5% |
| 20 mg/kg | 7.58 ± 0.18 | 7.08 ± 0.31 | −7% | −8% |
| 50 mg/kg | 7.94 ± 0.4 | 7.4 ± 0.51 | −7% | −4% |

Data represent the mean ± SE of 5-6 animals per group.

TABLE 6-2 ipGTT following Chlorthalidone treatment in DIO mice

| Treatment | AUC Day −1 (mM · min) | AUC Day 13 (mM · min) | Delta AUC Treatment Day 13 vs Day −1 | AUC Treatment vs Vehicle Day 13 |
|---|---|---|---|---|
| Vehicle | 1291 ± 175 | 1288 ± 167 | 0% | 0% |
| 10 mg/kg | 1439 ± 137 | 1660 ± 137 | 15% | 29% |
| 20 mg/kg | 1416 ± 110 | 1263 ± 75 | −11% | −2% |
| 50 mg/kg | 1398 ± 87 | 1512 ± 46 | 8% | 17% |

Data represent the mean ± SE of 5-6 animals per group.

Example 7. Effect of Furosemide on Fasting Blood Glucose Levels in Diet-Induced Obese Mice (*Mus Musculus*)

Compound Preparation and Administration
Dosing Solutions of the Test Articles:

Furosemide dosing solutions were prepared fresh on each dosing day and stored at room temperature, protected from light. The compound was formulated in sterile vehicle: Saline:PEG400 1:1 v/v.

Animals

Male C57Bl/6J mice were treated as for Example 5.

Treatment

During the last two weeks animals in groups of 6 were treated with doses selected from: vehicle, Furosemide 10 mg/kg, 20 mg/kg and 50 mg/kg in vehicle by oral gavage (5 µl per gram of body weight) using feeding tubes 18 ga (1.2 mm)*38 mm from Instech Solomon (Plymouth, USA).

Fasting Plasma Glucose (FPG) Concentration

The fasting plasma glucose levels of the animals was tested prior to commencement of the study and on day 13 of dosing as for Example 5. The results are presented in Table 7-1 and indicate that fursemide has no beneficial effect on fasting plasma glucose.

Body Weight

Treatment with furosemide resulted in substantial body weight loss in the animals, consistent with a toxic effect. The animals treated with 100 mg/kg/d lost ~6 g in 5 days, and had to be euthanized. The animals treated with 10-50 mg/kg/d lost between 4 and 6 g throughout the study.

TABLE 7-1

Fasting plasma glucose during Furosemide treatment in DIO mice

| Treatment | FPG Day −1 (mM) | FPG Day 13 (mM) | Delta FPG Treatment Day 13 vs Day −1 | FPG Treatment vs Vehicle Day 13 |
|---|---|---|---|---|
| Vehicle | 7.28 ± 0.3 | 8.68 ± 0.3 | 19% | 0% |
| 10 mg/kg | 7.28 ± 0.3 | 9.02 ± 0.4 | 24% | 4% |
| 20 mg/kg | 7.4 ± 0.4 | 8.50 ± 0.4 | 15% | −2% |
| 50 mg/kg | 6.78 ± 0.3 | 8.16 ± 0.6 | 20% | −6% |

Data represent the mean ± SE of 5-6 animals per group.

Example 8. Effect of Methazolamide, Metformin and Methazolamide/Metformin on Fasting Blood Glucose Levels in Diet-Induced Obese Mice (*Mus Musculus*)

(Reference to "metformin" means metformin hydrochloride)

Compound Preparation and Administration

Dosing Solutions of the Test Articles:

Sub-optimal fasting plasma glucose lowering doses for methazolamide and metformin were predetermined (10 mg/kg and 300 mg/kg respectively). Methazolamide. Metformin and Methazolamide/Metformin were prepared fresh on each dosing day and stored at room temperature, protected from light. The compound was formulated in sterile vehicle: NMP:PEG300:Saline (1:2:17, v/v). Stock solutions were prepared by dissolving the compound in NMP: PEG300(1:2, v/v). Saline was added to the stock solution prior to administration of the compound. The solutions were mixed by vortexing immediately prior to dosing to ensure a homogeneous suspension of the compound.

Animals

Male C57Bl/6J mice were treated as for Example 5.

Treatment

During the last two weeks animals in groups of 6 were treated with doses selected from: vehicle, Methazolamide 10 mg/kg, Metformin 300 mg/kg, Methazolamide/Metformin 10 mg/kg and 300 mg/kg in vehicle by oral gavage (5 µl per gram of body weight) using feeding tubes 18 ga (1.2 mm)*38 mm from Instech Solomon (Plymouth, USA).

Fasting Plasma Glucose (FPG) Concentration

The fasting plasma glucose levels of the animals was tested prior to commencement of the study and on day 13 of dosing as for Example 5. The results are presented in Table 8-1 and Table 8-2.

The data in Table 8-1 showed that treatment with combination Metformin/Methazolamide reduced the fasting plasma glucose levels of diet-induced obese mice and that this reduction was greater than that achieved by treatment with sub-optimal doses of either Metformin or Methazolamide alone.

The data in Table 8-2 showed that treatment with combination Metformin/Methazolamide improved the glucose tolerance of diet-induced obese mice and that this improvement was greater than that achieved by treatment with sub-optimal doses of either Metformin or Methazolamide alone.

TABLE 8-1

Fasting plasma glucose during Methazolamide, Metformin or Combined Methazolamide/Metformin treatment in DIO mice

| Treatment | FPG Day −1 (mM) | FPG Day 13 (mM) | Delta FPG Treatment Day 13 vs Day −1 | Delta FPG Treatment vs Vehicle Day 13 |
|---|---|---|---|---|
| Vehicle | 6.3 ± 0.3 | 7.6 ± 0.3 | 20%[1] | 0% |
| Methazolamide 10 mg/kg | 6.1 ± 0.5 | 6.6 ± 0.4 | 8% | −12% |
| Metformin 300 mg/kg | 6.1 ± 0.6 | 6.8 ± 0.4 | 11% | −11% |
| Methazolamide 10 mg/kg AND Metformin 300 mg/kg | 6.5 ± 0.4 | 6.1 ± 0.3 | −6% | −19%[2] |

Data represent the mean ± SE of 5-6 animals per group;
[1] $p = 0.01$;
[2] $p = 0.005$

TABLE 8-2 ipGTT during Methazolamide, Metformin or Combined Methazolamide/Metformin treatment in DIO mice

| Treatment | AUC Day −1 (mM · min) | AUC Day 13 (mM · min) | Delta AUC Day 13 vs Day −1 | AUC Day 13 Treat vs Veh |
|---|---|---|---|---|
| Vehicle | 1186 ± 73 | 1206 ± 69 | 2% | 0% |
| Methazolamide 10 mg/kg | 1190 ± 62 | 1131 ± 95 | −5% | −6% |
| Metformin 300 mg/kg | 1171 ± 81 | 1307 ± 91 | 12% | 8% |
| Methazolamide 10 mg/kg AND Metformin 300 mg/kg | 1222 ± 80 | 1072 ± 108 | −12% | −11% |

Data represent the mean ± SE of 5-6 animals per group.

Example 9. Effect of Methazolamide, Metformin and Methazolamide/Metformin on Fasting Blood Glucose Levels in Db/Db Mice (*Mus Musculus*)

(Reference to "metformin" means metformin hydrochloride)

The db/db mouse model comprises mice with a homozygous mutation of the leptin receptor gene that ablates leptin signalling in the hypothalamus and elsewhere. The db/db mouse model is commonly used to study the genetic and physiological mechanisms of obesity and type II diabetes. Unlike DIO mice in which obesity and insulin resistance is induced by feeding a high caloric diet, db/db mice spontaneously develop severe hyperglycemia (>20 mM), morbid obesity (Fat >35% body weight) and diabetes, even when fed with standard laboratory chow. Leptin acts through the leptin receptor to control whole-body energy homeostasis by regulating both appetite and energy expenditure. Loss of function of the leptin receptor gene results in hyperphagia and slower metabolism, leading to obesity and eventually diabetes. Diabetes in this model is characterised by fasting plasma glucose levels >20 mM and the magnitude of the reduction in fasting plasma glucose concentrations following treatment with a compound is taken as a measure of the efficacy of that compound in improving the animal's glucose metabolism.

Compound Preparation and Administration

Dosing solutions of the test articles: Methazolamide, Metformin and Methazolamide/Metformin were prepared fresh on each dosing day and stored at room temperature, protected from light. The compound was formulated in sterile vehicle: NMP:PEG300:Saline (1:2:17, v/v). Stock solutions were prepared by dissolving the compound in NMP:PEG300 (1:2, v/v). Saline was added to the stock solution prior to administration of the compound. The solutions were mixed by vortexing immediately prior to dosing to ensure a homogeneous suspension of the compound.

Animals

Male C57Bl/6J db/db mice were obtained at 10 weeks of age from Animal Resources Centre (Canning Vale, Western Australia). Animals were individually housed and allowed free movement and ad libitum access to water and food. Animals were maintained on a 12 hour light (6 am-6 pm) and 12 hour dark (6 pm-6 am) cycle. Animals were monitored daily. Body weight, food and water intake were recorded 3 times a week. Mice were fed a standard chow diet, and used after a two week acclimatisation period.

Treatment

Animals in groups of 6 were treated with doses selected from: vehicle, Methazolamide 20 mg/kg, Metformin 300 mg/kg, Methazolamide/Metformin 20 mg/kg and 300 mg/kg in vehicle by oral gavage (5 µl per gram of body weight) using feeding tubes 18 ga (1.2 mm)*38 mm from Instech Solomon (Plymouth, USA).

Fasting Plasma Glucose Concentration

The fasting plasma glucose levels of the animals was tested prior to commencement of the study and then every 3-4 days during dosing. The animals were fasted for a period of 4 hours after dosing and prior to the taking of a blood sample via a tail nick. Blood glucose levels were monitored using commercially available glucometers (Accuchek Advantage, Roche) based on the electric current generated when a blood drop is spotted on a test strip resulting in conversion of the glucose present in the sample to gluconolactone by the glucose dehydrogenase enzyme, in the presence of the coenzyme (PQQ). The results are presented in Table 9-1 and Table 9-2.

The data in Table 9-1 showed that treatment with Methazolamide reduced the fasting plasma glucose levels of db/db mice after 8 days of treatment.

The data in Table 9-2 showed that treatment with Methazolamide reduced the fasting plasma glucose levels of db/db mice after 18 days of treatment The data in Table 9-1 showed that treatment with combination Metformin/Methazolamide reduced the fasting plasma glucose levels of db/db mice after 8 days of treatment, and that this reduction was greater than that achieved by treatment with either Metformin or Methazolamide alone.

The data in Table 9-2 showed that treatment with combination Metformin/Methazolamide reduced the fasting plasma glucose levels of db/db mice after 18 days of treatment, and that this reduction was greater than that achieved by treatment with either Metformin or Methazolamide alone.

Body Weight

There was no difference in body weight between the Vehicle and Methazolamide treated groups at Day 0, Day 8 or Day 18, indicating that the effects of Methazolamide treatment on glucose metabolism were not secondary to changes in body weight.

There was no difference in body weight between the Vehicle and combination Metformin/Methazolamide treated groups at Day 0, Day 8 or Day 18, indicating that the effects of combination Metformin/Methazolamide treatment on glucose metabolism were not secondary to changes in body weight.

TABLE 9-1

Fasting plasma glucose during Methazolamide, Metformin or Combined Methazolamide/Metformin treatment at Day 8 in db/db mouse model

| Treatment | FPG Day 0 (mM) | FPG Day 8 (mM) | Delta FPG Treatment Day 8 vs Day 0 | FPG Treatment vs Vehicle Day 8 |
|---|---|---|---|---|
| Vehicle | 23.91 ± 2.0 | 23.37 ± 1.4 | −2% | 0% |
| Methazolamide 20 mg/kg | 23.93 ± 1.6 | 16.30 ± 1.8 | −32%[1] | −30%[4] |
| Metformin 300 mg/kg | 23.86 ± 1.4 | 19.10 ± 2.1 | −20%[2] | −18% |
| Methazolamide 20 mg/kg AND Metformin 300 mg/kg | 23.63 ± 1.7 | 12.46 ± 1.9 | −47%[3] | −47%[5] |

[1] p = 0.0005 paired ttest;
[2] p = 0.02 paired ttest;
[3] p = 0.0003 paired ttest;
[4] p = 0.01 unpaired ttest;
[5] p = 0.0007 unpaired ttest

TABLE 9-2

Fasting plasma glucose during Methazolamide, Metformin or Combined Methazolamide/Metformin treatment at Day 18 in db/db mouse model

| Treatment | FPG Day 0 (mM) | FPG Day 18 (mM) | Delta FPG Treatment Day 18 vs Day 0 | FPG Treatment vs Vehicle Day 18 |
|---|---|---|---|---|
| Vehicle | 23.91 ± 2.0 | 27.27 ± 1.3 | 14% | 0% |
| Methazolamide 20 mg/kg | 23.93 ± 1.6 | 17.00 ± 2.5 | −29%[1] | −38%[3] |
| Metformin 300 mg/kg | 23.86 ± 1.4 | 20.01 ± 1.8 | −16% | −27%[4] |
| Methazolamide 20 mg/kg AND Metformin 300 mg/kg | 23.63 ± 1.7 | 13.20 ± 1.9 | −44%[2] | −52%[4] |

[1] p = 0.0009 paired ttest;
[2] p = 0.02 paired ttest;
[3] p = 0.003 unpaired ttest;
[4] p = 0.009 unpaired ttest;
[5] p = 0.00004 unpaired ttest Example 10. Effect of Acetazolamide on Fasting Blood Glucose Levels in Diet-Induced Obese Mice (*Mus Musculus*)

Compound Preparation and Administration

Dosing Solutions of the Test Articles:

Acetazolamide dosing solutions were prepared fresh on each dosing day and stored at room temperature, protected from light. The compound was formulated in sterile vehicle: Saline:PEG400 65:35 v/v.

Animals

Male C57Bl/6J mice were obtained at 8 weeks of age from Animal Resources Centre (Canning Vale, Western Australia). Animals were individually housed and allowed free movement and ad libitum access to water and food. Animals were maintained on a 12 hour light (6 am-6 pm) and 12 hour dark (6 pm-6 am) cycle. Animals were monitored daily. Body weight, food and water intake were recorded 3 times a week. After two weeks acclimatizing, mice were fed a high fat rich diet (SFO4-001, Specialty feeds, Glen Forrest, Wash., Australia with a total energy density of 4.7 kcal/g. Caloric distribution in the diet was 20% from protein, 35% from carbohydrates, and 45% from fat) for 12 weeks.

Treatment

During the last two weeks animals in groups of 6 were treated b.i.d. (at 9:00 AM and 16:00 PM) with doses selected from: vehicle: Acetazolamide 10 mg/kg, 20 mg/kg, 50 mg/kg in vehicle by oral gavage (5 µl per gram of body weight) using feeding tubes 18 ga (1.2 mm)*38 mm from Instech Solomon (Plymouth, USA).

Fasting Plasma Glucose (FPG) Concentration

The fasting plasma glucose levels of the animals was tested prior to commencement of the study and on day 13 of dosing. The animals were fasted for a period of 4 hours after dosing and prior to the taking of a blood sample via a tail nick. Blood glucose levels were monitored using commercially available glucometers (Accuchek Advantage, Roche) based on the electric current generated when a blood drop is spotted on a test strip resulting in conversion of the glucose present in the sample to gluconolactone by the glucose dehydrogenase enzyme, in the presence of the coenzyme (PQQ). The results are presented in Table 10-1 and Table 10-2.

The data in Table 10-1 showed that treatment with Acetazolamide reduced the fasting plasma glucose levels of diet-induced obese mice.

The date in Table 10-2 showed that treatment with Acetazolamide increased the glucose tolerance of diet-induced obese mice.

Body Weight

There was no difference in body weight between any of the treated groups at either Day 0 or Day 13, indicating that the effects of Acetazolamide on glucose metabolism were not secondary to changes in body weight.

TABLE 10-1

Fasting plasma glucose during Acetazolamide treatment in DIO mice

| Treatment | FPG Day −1 (mM) | FPG Day 13 (mM) | Delta FPG Treatment Day 13 vs Day −1 | FPG Treatment vs Vehicle Day 13 |
| --- | --- | --- | --- | --- |
| Vehicle | 6.4 ± 0.43 | 6.34 ± 0.15 | −1% | 0% |
| 10 mg/kg | 6.35 ± 0.5 | 5.76 ± 0.43 | −9% | −9% |
| 20 mg/kg | 6.32 ± 0.42 | 5.46 ± 0.32 | −14%[2] | −14%[1] |
| 50 mg/kg | 6.62 ± 0.38 | 6.28 ± 0.31 | −5% | −1% |

[1] $p < 0.03$,
[2] $p = 0.08$
Data represent the mean ± SE of 5-6 animals per group.

TABLE 10-2 ipGTT following Acetazolamide treatment in DIO mice

| Treatment | AUC Day −1 (mM · min) | AUC Day 13 (mM · min) | Delta AUC Treatment Day 13 vs Day −1 | AUC Treatment vs Vehicle Day 13 |
| --- | --- | --- | --- | --- |
| Vehicle | 1300 ± 60 | 1211 ± 109 | −7% | 0% |
| 10 mg/kg | 1342 ± 88 | 944 ± 26 | −30%[1] | −22%[2] |
| 20 mg/kg | 1340 ± 68 | 902 ± 98 | −33%[1] | −25%[3] |
| 50 mg/kg | 1323 ± 109 | 1020 ± 144 | −23%[2] | −15% |

[1] $p < 0.01$,
[2] $p < 0.05$,
[3] $p = 0.068$
Data represent the mean ± SE of 5-6 animals per group.

We claim:

1. A method of treating fatty liver disease, comprising: administering to a subject a compound of Formula (III),

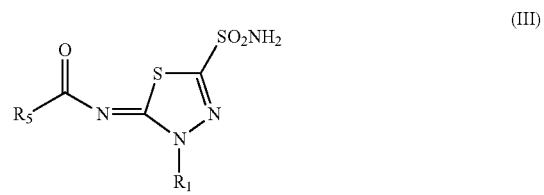

(III)

wherein $R_1$ is selected from hydrogen, $C_{1-6}$alkyl, $C(O)C_{1-6}$alkyl and $(CH_2)_n$ phenyl, where n is 1, 2, 3, 4, 5 or 6 and phenyl may be unsubstituted or optionally substituted by one or more substituents independently selected from $C_{1-6}$alkyl, halo, hydroxy, hydroxy$C_{1-6}$alkyl, $C_{1-6}$alkoxy, $C_{1-6}$ alkoxy$C_{1-6}$alkyl, $C_{1-6}$alkoxy$C_{1-6}$alkoxy, halo$C_{1-6}$alkyl, halo$C_{1-6}$alkoxy, cyano, nitro, $OC(O)C_{1-6}$ alkyl, $NH_2$, $NHC_{1-6}$alkyl, $NHC(O)C_{1-6}$alkyl and $NC_{1-6}$alkyl$C_{1-6}$alkyl; and $R_5$ is selected from hydrogen, $C_{1-6}$alkyl, $C(O)C_{1-6}$alkyl, and $(CH_2)_n$ phenyl, where n is 1, 2, 3, 4, 5 or 6 and phenyl may be unsubstituted or substituted by one or more substituents independently selected from $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$ alkoxy, halo$C_{1-6}$ alkyl, halo$C_{1-6}$alkoxy, cyano, nitro, $OC(O)C_{1-6}$alkyl, $NH_2$, $NHC_{1-6}$alkyl, $NHC(O)C_{1-6}$ alkyl and $NC_{1-6}$alkyl$C_{1-6}$alkyl, or a pharmaceutically acceptable salt, solvate or prodrug thereof.

2. The method of claim 1, wherein $R_1$ is $CH_3$ and $R_5$ is $CH_3$.

3. The method of claim 1, wherein the compound of Formula (III) is administered at a dose of from 10 to 100 mg per day.

4. The method of claim 1, wherein the compound of Formula (III) is in the form of a capsule, sachets, or tablet.

5. The method of claim 1, wherein the subject has a fasting state blood glucose level of about 6.1 mmol/L or greater.

* * * * *